(12) United States Patent
Doan et al.

(10) Patent No.: US 11,844,947 B2
(45) Date of Patent: Dec. 19, 2023

(54) SPINAL CORD STIMULATION OCCURRING USING MONOPHASIC PULSES OF ALTERNATING POLARITIES AND PASSIVE CHARGE RECOVERY

(71) Applicant: Boston Scientific Neuromodulation Corporation, Valencia, CA (US)

(72) Inventors: Que T. Doan, West Hills, CA (US); Luca Antonello Annecchino, London (GB); Ismael Huertas Fernandez, Madrid (ES)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 204 days.

(21) Appl. No.: 16/741,196

(22) Filed: Jan. 13, 2020

(65) Prior Publication Data

US 2020/0147392 A1 May 14, 2020

Related U.S. Application Data

(63) Continuation-in-part of application No. 16/738,786, filed on Jan. 9, 2020, which is a continuation-in-part
(Continued)

(51) Int. Cl.
*A61N 1/36* (2006.01)
*A61N 1/02* (2006.01)

(52) U.S. Cl.
CPC ......... *A61N 1/36175* (2013.01); *A61N 1/025* (2013.01); *A61N 1/36062* (2017.08); *A61N 1/36185* (2013.01)

(58) Field of Classification Search
CPC .............. A61N 1/36132; A61N 1/0551; A61N 1/36178; A61N 1/37211; A61N 1/36062;
(Continued)

(56) References Cited

U.S. PATENT DOCUMENTS 4,520,825 A 6/1985 Thompson et al.
6,181,969 B1 1/2001 Gord
(Continued)

FOREIGN PATENT DOCUMENTS

CN 202933390 5/2013
EP 2923727 9/2015
WO 2017/106539 6/2017

OTHER PUBLICATIONS

McKay CM, Henshall KR. The perceptual effects of interphase gap duration in cochlear implant stimulation. Hear Res. Jul. 2003; 181 (1-2):94-9. doi: 10.1016/s0378-5955(03)00177-1. PMID: 12855367. (Year: 2003).*
(Continued)

*Primary Examiner* — Ankit D Tejani
*Assistant Examiner* — Ranjani Mari Sundaresan
(74) *Attorney, Agent, or Firm* — Lewis & Reese, PLLC

(57) ABSTRACT

New waveforms for use in an implantable pulse generator or external trial stimulator are disclosed which mimic actively-driven biphasic pulses, and which are particularly useful for issuing low frequencies pulses. The waveforms comprise at each electrode interleaved first and second pulses. Each first pulse comprises a first monophasic pulse and a first passive charge recovery period. Each second pulse comprises a second monophasic pulse with a polarity opposite the first monophasic pulse and a second passive charge recovery period. Preferably, the amplitudes and pulse widths of the first and second monophasic pulses are equal, or at least charge balanced at each electrode. The first and second monophasic pulses mimic the functionality of a symmetric biphasic pulse, with the first monophasic pulse mimicking the functionality of the biphasic pulse's first phase, and the with the second monophasic pulse mimicking the functionality of the biphasic pulse's second phase.

18 Claims, 11 Drawing Sheets

Related U.S. Application Data of application No. 16/657,560, filed on Oct. 18, 2019, which is a continuation-in-part of application No. 16/460,640, filed on Jul. 2, 2019, and a continuation-in-part of application No. 16/460,655, filed on Jul. 2, 2019, now Pat. No. 11,338,127, said application No. 16/657,560 is a continuation-in-part of application No. 16/100,904, filed on Aug. 10, 2018, now Pat. No. 10,576,282.

(60) Provisional application No. 62/802,998, filed on Feb. 8, 2019, provisional application No. 62/803,330, filed on Feb. 8, 2019, provisional application No. 62/693,543, filed on Jul. 3, 2018, provisional application No. 62/544,656, filed on Aug. 11, 2017.

(58) Field of Classification Search
CPC ............ A61N 1/36146; A61N 1/36175; A61N 1/36128; A61N 1/36135; A61N 1/36185
See application file for complete search history.

(56) References Cited

U.S. PATENT DOCUMENTS

| | | |
|---|---|---|
| 6,246,912 B1 | 6/2001 | Sluijter et al. |
| 6,516,227 B1 | 2/2003 | Meadows et al. |
| 6,560,490 B2 | 5/2003 | Grill et al. |
| 7,603,177 B2 | 10/2009 | Sieracki et al. |
| 7,734,340 B2 | 6/2010 | De Ridder |
| 7,890,182 B2 | 2/2011 | Parramon et al. |
| 8,180,451 B2 | 5/2012 | Hickman et al. |
| 8,224,453 B2 | 7/2012 | De Ridder |
| 8,359,102 B2 | 1/2013 | Alataris et al. |
| 8,364,273 B2 | 1/2013 | De Ridder |
| 8,401,655 B2 | 3/2013 | De Ridder |
| 8,515,546 B2 | 8/2013 | Goddard et al. |
| 8,606,362 B2 | 12/2013 | He et al. |
| 8,620,436 B2 | 12/2013 | Parramon et al. |
| 8,712,533 B2 | 4/2014 | Alataris et al. |
| 8,712,534 B2 | 4/2014 | Wei |
| 8,774,927 B2 | 7/2014 | DeRidder |
| 8,792,988 B2 | 7/2014 | Alataris et al. |
| 8,897,870 B2 | 11/2014 | De Ridder |
| 8,934,981 B2 | 1/2015 | De Ridder |
| 9,259,574 B2 | 2/2016 | Aghassian et al. |
| 9,327,125 B2 | 5/2016 | Alataris et al. |
| 9,333,357 B2 | 5/2016 | Alataris et al. |
| 9,358,391 B2 | 6/2016 | Zhu et al. |
| 9,446,243 B2 | 9/2016 | Marnfeldt et al. |
| 9,462,398 B2 | 10/2016 | DeRidder |
| 9,480,842 B2 | 11/2016 | Alataris et al. |
| 9,511,227 B2 | 12/2016 | Biele et al. |
| 9,511,232 B2 | 12/2016 | Biele et al. |
| 9,526,899 B2 | 12/2016 | Biele et al. |
| 9,550,062 B2 | 1/2017 | Khalil et al. |
| 9,656,077 B2 | 5/2017 | De Ridder |
| 9,656,081 B2 | 5/2017 | Feldman et al. |
| 9,737,718 B2 | 8/2017 | Biele et al. |
| 9,789,252 B2 | 10/2017 | Gerber et al. |
| 2006/0015153 A1 | 1/2006 | Gliner et al. |
| 2006/0173493 A1 | 8/2006 | Armstrong et al. |
| 2008/0319497 A1 | 12/2008 | Griffith et al. |
| 2010/0023090 A1 | 1/2010 | Jaax et al. |
| 2010/0030299 A1* | 2/2010 | Covalin ................ A61B 18/00 607/46 |
| 2010/0274312 A1 | 10/2010 | Alataris et al. |
| 2011/0106214 A1 | 5/2011 | Carbunaru et al. |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2012/0172946 A1 | 7/2012 | Alataris et al. |
| 2013/0053923 A1 | 2/2013 | Jaax et al. |
| 2013/0268026 A1 | 10/2013 | Rao et al. |
| 2013/0289665 A1 | 10/2013 | Marnfeldt et al. |
| 2014/0277251 A1 | 9/2014 | Gerber et al. |
| 2014/0364919 A1 | 12/2014 | Doan |
| 2015/0080982 A1 | 3/2015 | Funderburk |
| 2015/0157861 A1 | 6/2015 | Aghassian |
| 2015/0231402 A1 | 8/2015 | Aghassian |
| 2015/0335893 A1 | 11/2015 | Parker |
| 2015/0360038 A1 | 12/2015 | Zottola et al. |
| 2016/0082265 A1 | 3/2016 | Moffitt et al. |
| 2016/0114166 A1 | 4/2016 | Kaula et al. |
| 2016/0144183 A1 | 5/2016 | Marnfeldt |
| 2016/0144184 A1* | 5/2016 | Marnfeldt .......... A61N 1/36125 607/63 |
| 2016/0158551 A1 | 6/2016 | Kent et al. |
| 2016/0184591 A1 | 6/2016 | Feldman et al. |
| 2016/0317815 A1 | 11/2016 | Doan et al. |
| 2016/0361543 A1 | 12/2016 | Kaula et al. |
| 2016/0367822 A1 | 12/2016 | Parramon |
| 2017/0056642 A1 | 3/2017 | Moffitt et al. |
| 2017/0106197 A1 | 4/2017 | Wechter et al. |
| 2017/0165490 A1 | 6/2017 | Wechter |
| 2017/0173335 A1 | 6/2017 | Min et al. |
| 2017/0189685 A1 | 7/2017 | Steinke et al. |
| 2018/0043172 A1 | 2/2018 | Serrano Carmona |
| 2018/0071513 A1 | 3/2018 | Weiss et al. |
| 2018/0071520 A1 | 3/2018 | Weerakoon et al. |
| 2018/0071527 A1 | 3/2018 | Feldman et al. |
| 2018/0104468 A1 | 4/2018 | Marnfeldt et al. |
| 2018/0104493 A1 | 4/2018 | Doan et al. |
| 2018/0140831 A1* | 5/2018 | Feldman ............... A61N 1/3605 |
| 2018/0272124 A1 | 9/2018 | Kibler et al. |
| 2019/0046800 A1 | 2/2019 | Doan et al. |
| 2019/0083796 A1 | 3/2019 | Weerakoon et al. |
| 2019/0175915 A1 | 6/2019 | Brill et al. |
| 2019/0184180 A1 | 6/2019 | Zhang et al. |
| 2019/0209844 A1 | 7/2019 | Esteller et al. |
| 2019/0290900 A1 | 9/2019 | Esteller et al. |
| 2019/0329024 A1 | 10/2019 | Kothandaraman et al. |
| 2019/0329025 A1 | 10/2019 | Moffitt et al. |
| 2019/0329039 A1 | 10/2019 | Marnfeldt et al. |
| 2019/0344083 A1 | 11/2019 | Marnfeldt et al. |
| 2019/0366104 A1 | 12/2019 | Doan et al. |
| 2020/0009367 A1 | 1/2020 | Huertas Fernandez et al. |
| 2020/0009394 A1 | 1/2020 | Huertas Fernandez et al. |

OTHER PUBLICATIONS

International Search Report and Written Opinion regarding corresponding PCT Application No. PCT/US2020/013332, dated Apr. 15, 2020.

U.S. Appl. No. 62/860,627, filed Jun. 12, 2019, Esteller et al.

U.S. Appl. No. 16/657,560, filed Oct. 18, 2019, Moffitt et al.

L. Kapural et al., "Novel 10-kHz High-frequency Therapy (HF10 Therapy) Is Superior to Traditional Low-frequency Spinal Cord Stimulation for the Treatment of Chronic Back and Leg Pain," Anesthesiology 2015; 123:851-60 (Oct. 2015).

S. Thomson et al., "The PROCO Randomised Controlled Trial: Effects of Pulse Rate on Clinical Outcomes in Kilohertz Frequency Spinal Cord Stimulation—a Multicentre, Double-blind, Crossover Study," presented at the International Neuromodulation Society (INS) Meeting on May 31, 2017.

E.C. Celik et al., "The effect of low-frequency TENS in the treatment of neuropathic pain in patients with spinal cord injury," Spinal Cord 51:34-337 (2013).

Y. Maeda et al., "Low frequencies, but not high frequencies of bi-polar spinal cord stimulation reduce cutaneous and muscle hyperalgesia induced by nerve injury," Pain 138:143-152 (2008).

S. Thomson et al., "Neural Dosing and Energy Requirements in Kilohertz Frequency Spinal Cord Stimulation (SCS)," poster presented at the International Neuromodulation Society (INS) Meeting on May 31, 2017.

S. Paz et al., "Improved Efficacy of SCS Implants Using Multiple Waveforms and Field Shape Options," poster presented at the International Neuromodulation Society (INS) Meeting on May 31, 2017.

S. Paz et al., "Evaluation of Customized Field Shape for Subperception SCS in a Case Series of Chronic Pain Patients," poster presented at the North American Neuromodulation Society (NANS) Meeting on Jan. 11-14, 2018.

(56) References Cited

OTHER PUBLICATIONS

S.J. Thomson et al., "Effects of Rate on Analgesia in Kilohertz Frequency Spinal Cord Stimulation: Results of the PROCO Randomized Controlled Trial," Neuromodulation: Technology at the Neural Interface, vol. 21(1), pp. 67-76 (2018) (published on-line Dec. 8, 2017).

J.M. North et al., "Clinical Outcomes of 1 kHz Subperception Spinal Cord Stimulation in Implanted Patients With Failed Paresthesia-Based Stimulation: Results of a Prospective Randomized Controlled Trial," Neuromodulation: Technology at the Neural Interface, vol. 19(7), pp. 731-737 (2016).

Yearwood, Thomas, et al., Handout titled "A Prospective Comparison of Spinal Cord Stimulation (SCS) Using Dorsal Colunm Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.

Yearwood, Thomas, et al., Poster titled "A Prospective Comparison of Spinal Cord Stimulation (SCS) Using Dorsal Colunm Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 7 pages.

Yearwood, Thomas, "Neuropathic Extremity Paid and Spinal Cord Stimulation," Pain Medicine, vol. 7, No. S1, 2006, 6 pages.

\* cited by examiner

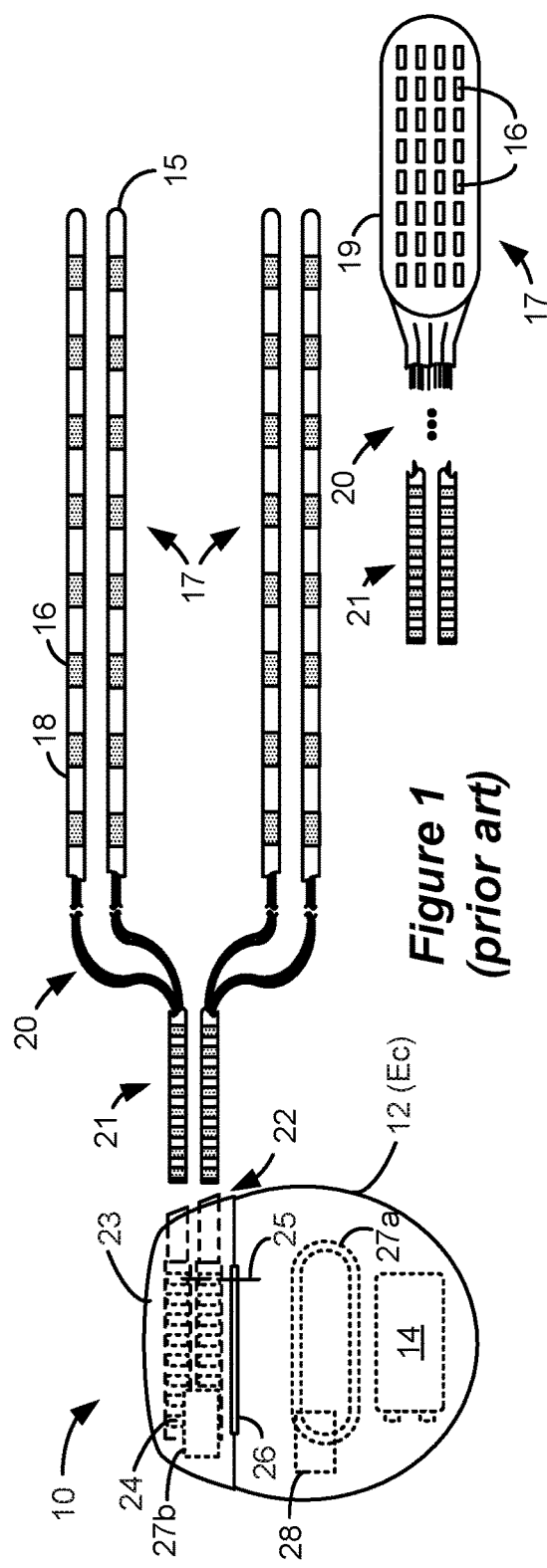
*Figure 1 (prior art)*
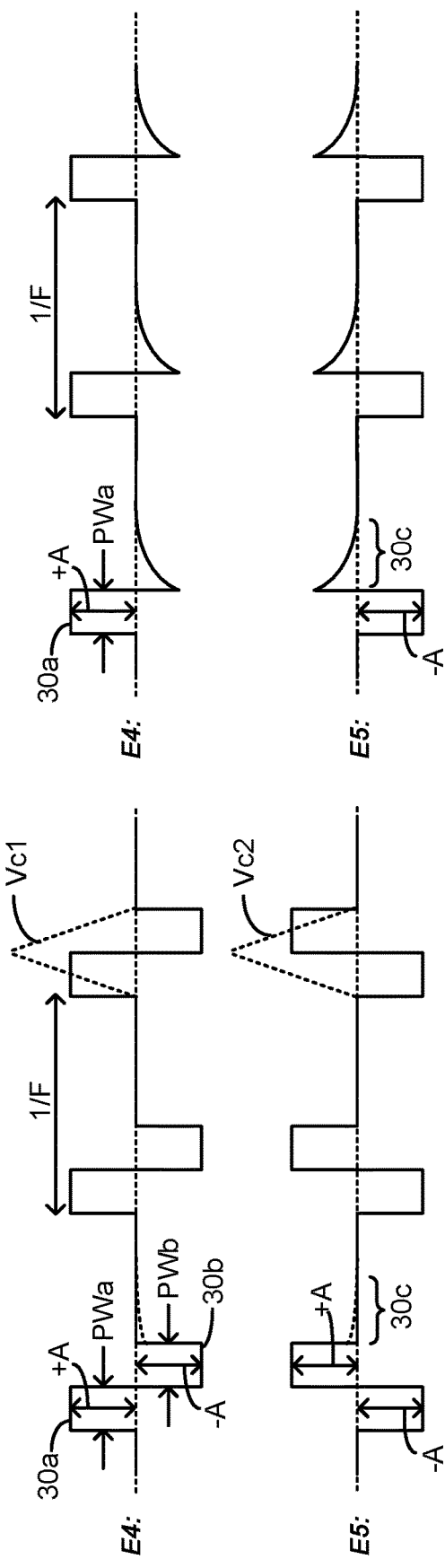
*Figure 2A (prior art)*
*Figure 2B (prior art)*

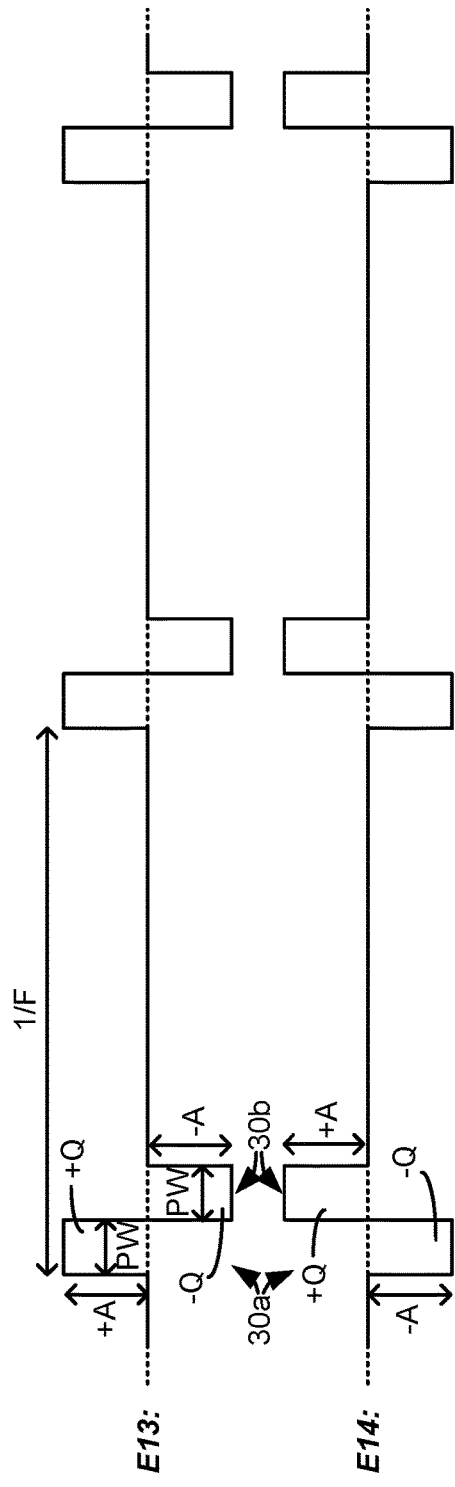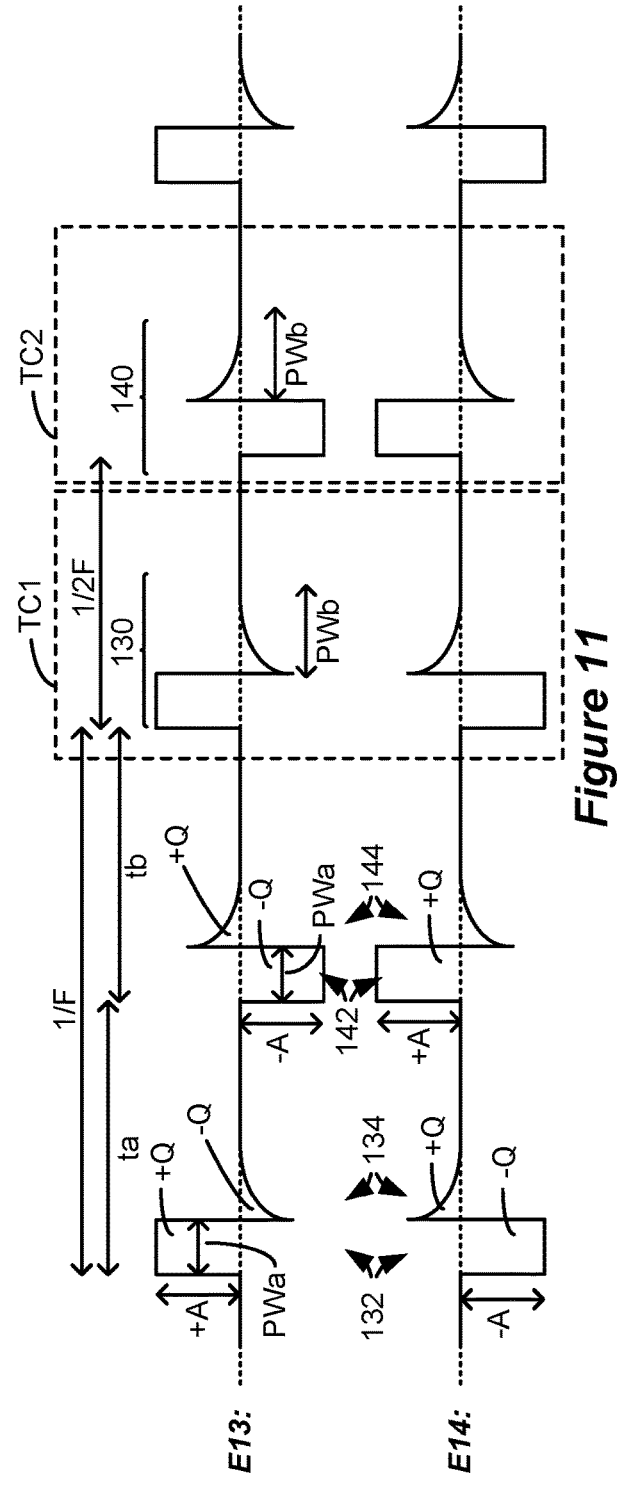

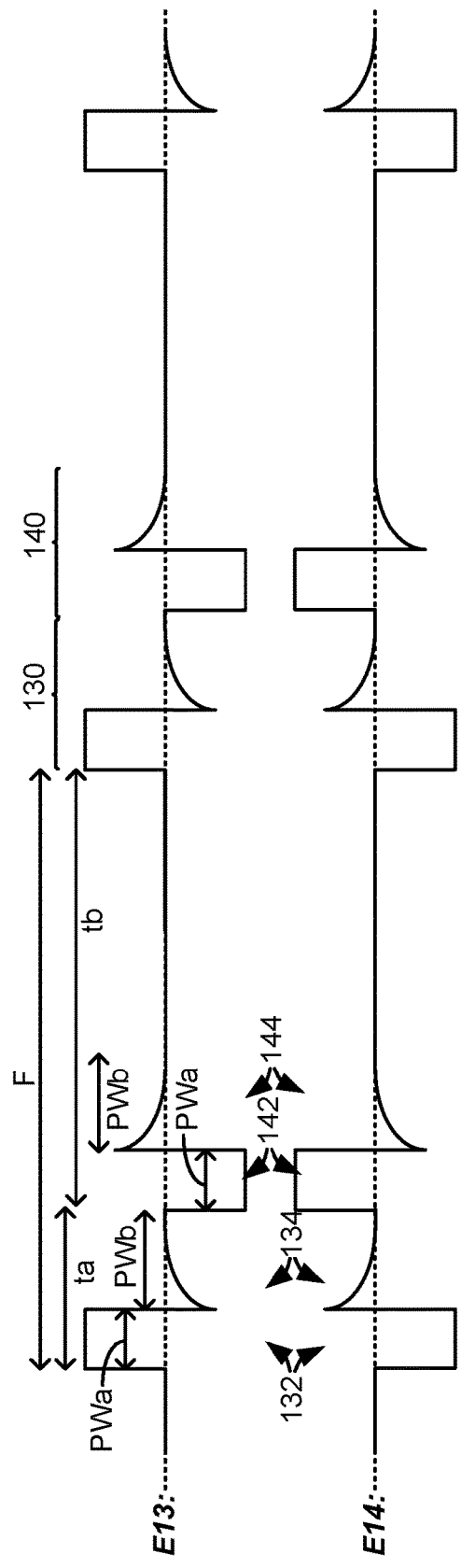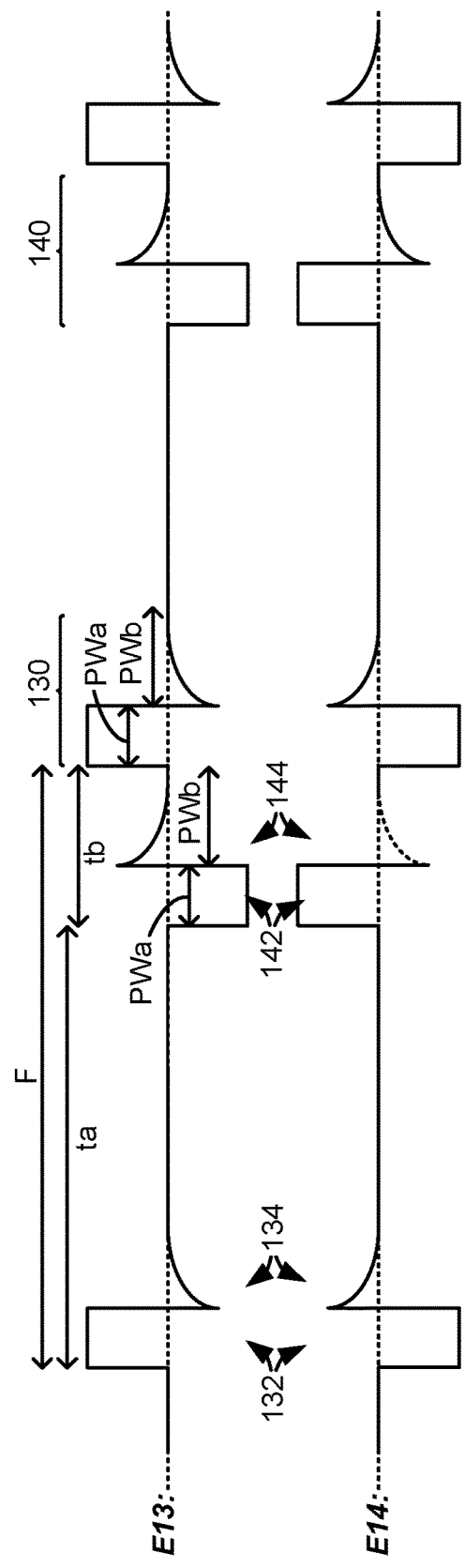

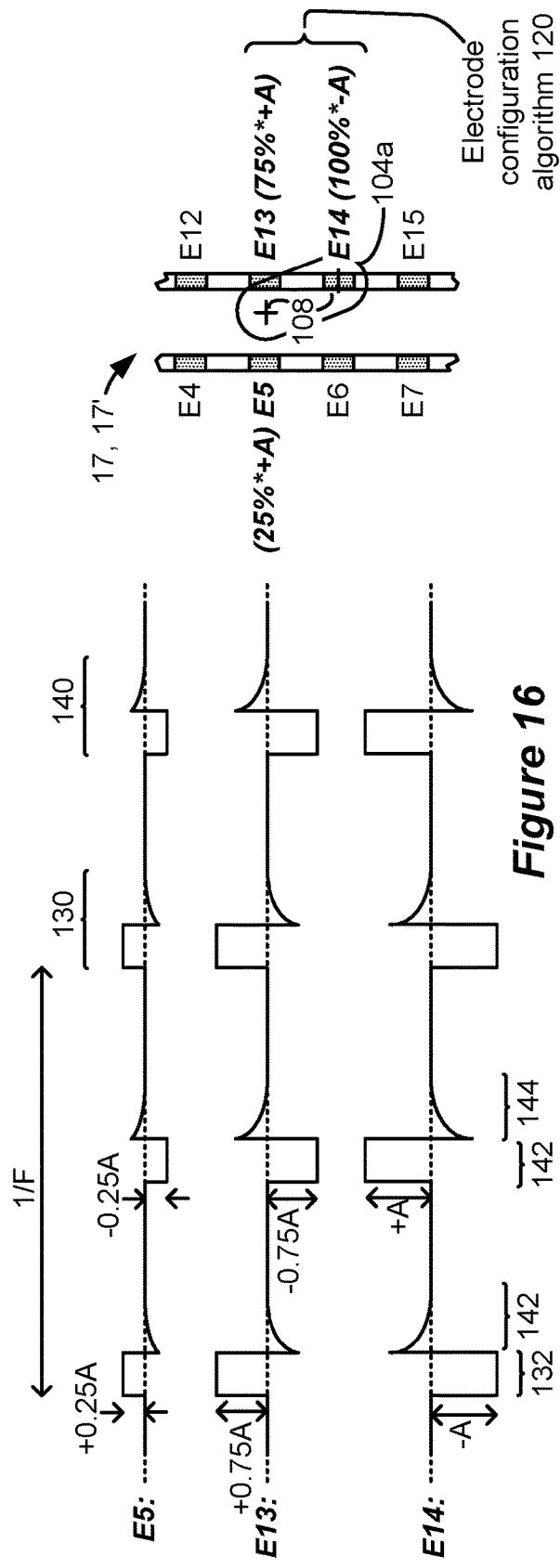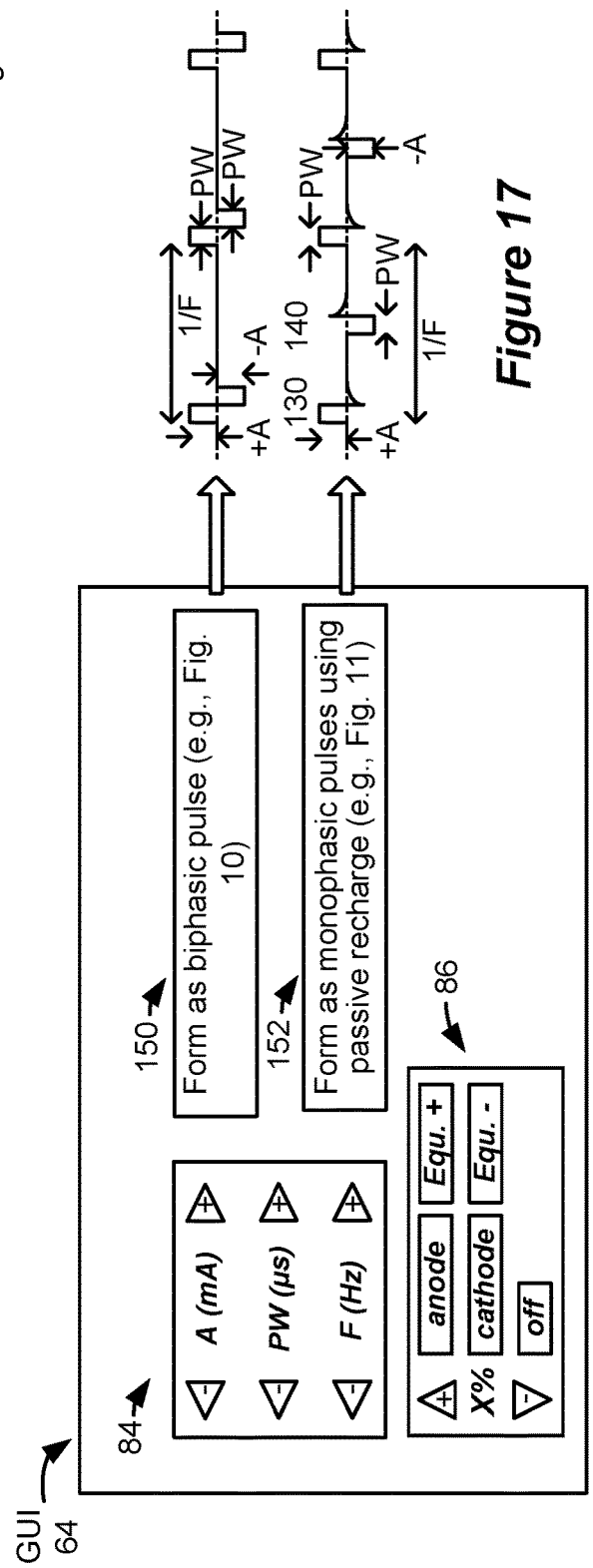

SPINAL CORD STIMULATION OCCURRING USING MONOPHASIC PULSES OF ALTERNATING POLARITIES AND PASSIVE CHARGE RECOVERY

CROSS-REFERENCE TO RELATED APPLICATIONS

This application is a non-provisional application of U.S. Provisional Patent Application Ser. No. 62/802,998, filed Feb. 8, 2019.

This application is also a continuation-in-part of U.S. patent application Ser. No. 16/738,786, filed Jan. 9, 2020, which is a continuation-in-part of U.S. patent application Ser. No. 16/657,560, filed Oct. 18, 2019, which is a continuation-in-part of U.S. patent application Ser. No. 16/100,904, filed Aug. 10, 2018, which is a non-provisional application of U.S. Provisional Patent Application Ser. Nos. 62/693,543, filed Jul. 3, 2018, and 62/544,656, filed Aug. 11, 2017;

U.S. patent application Ser. No. 16/460,640, filed Jul. 2, 2019, which is a non-provisional application of U.S. Provisional Patent Application Ser. No. 62/803,330, filed Feb. 8, 2019; and U.S. patent application Ser. No. 16/460,655, filed Jul. 2, 2019, which is a non-provisional application of U.S. Provisional Patent Application Ser. No. 62/803,330, filed Feb. 8, 2019.

Priority is claimed to these above-referenced applications, and all are incorporated by reference in their entireties.

FIELD OF THE INVENTION

This application relates to Implantable Medical Devices (IMDs), generally, Spinal Cord Stimulators, more specifically, and to methods of control of such devices.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SC S) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a typically conductive biocompatible device case 12 that holds the IPG's circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices used to program or monitor the IPG, such as a hand-held patient controller or a clinician's programmer described later with respect to FIG. 5. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, MICS, and the like.

Stimulation in IPG 10 is typically provided by pulses, as shown in FIGS. 2A and 2B. Stimulation parameters typically include the amplitude of the pulses (A; whether current or voltage); the frequency (F) of the pulses; the pulse width (PW) of the pulses (or its individual phases as described below); the electrodes 16 (E) activated to provide such stimulation; and the polarity (P) of such active electrodes, i.e., whether active electrodes are to act as anodes that source current to the tissue or cathodes that sink current from the tissue. These and possibly other stimulation parameters taken together comprise a stimulation program that the IPG 10 can execute to provide stimulation to a patient.

The pulses in FIG. 2A comprise two pulse phases 30a and 30b each actively driven by stimulation circuitry 28 shown in FIG. 3. During the first phase 30a, electrode E4 has been selected as an anode and thus sources a positive current of amplitude +A to the tissue, while electrode E5 has been selected as a cathode and thus sinks a corresponding negative current of amplitude −A from the tissue. However, more than one electrode may act as an anode at a given time, and more than one electrode may act as a cathode at a given time. Stimulation may also occur using the case electrode Ec, as shown in FIG. 3.

The pulses as shown in FIG. 2A, with two actively-driven phases 30a and 30b, are typically known as "biphasic" pulses, with phases 30a and 30b having opposite polarity. (A short interphase period may intervene between the two phases 30a and 30b during which no current flows, although this isn't shown). The use of biphasic pulses are useful in charge recovery, which can be necessary in light of capacitances in the current path established between the selected electrodes, as explained further below. Although not shown, each of the phases 30a and 30b could be broken up into a series of higher-frequency pulses, which is often referred to as a "burst" of pulses, as is well known.

The stimulation circuitry 28 as shown in FIG. 3 includes one or more current source circuits $40_i$ and one or more current sink circuits $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation. PDACs $40_1$ and NDACs $42_i$ can also comprise voltage sources. Although not shown, switching matrices can intervene between the one or more PDACs $40_1$ and the electrode nodes ei 39, and between the one or more NDACs $42_i$ and the electrode nodes. Switching matrices allows one or more of the PDACs or one or more of the NDACs to be connected to one or more anode or cathode electrode nodes at a given time.

The stimulation circuitry 28 is configured by the stimulation parameters, which may be provided to the stimulation circuitry 28 by controller circuitry 29 in the IPG 10. Controller circuitry 29 may comprise a microcontroller, microprocessor, microcomputer, an FPGA, other digital logic structures, etc., which is capable of executing instructions in an electronic device. Controller circuitry 29 may comprise a separate component, or may be integrated with an Application Specific Integrated Circuit (ASIC) that includes the stimulation circuitry 28 as well as other circuitry necessary to operate various function of the IPG 10. Proper control of the PDACs $40_i$ and NDACs $42_i$ via the stimulation parameters allows any of the electrodes 16 to act as anodes or cathodes to create a current I of the prescribed amplitude A through a patient's tissue, R, hopefully with good therapeutic effect. In the example shown, and during the first phase 30a in which electrodes E4 and E5 are selected as an anode and cathode respectively, PDAC $40_4$ and NDAC $42_5$ are activated and digitally programmed to produce the desired current, A, with the correct timing (e.g., in accordance with the prescribed frequency F and pulse width PWa). During the second phase 30b (PWb), PDAC $40_5$ and NDAC $42_4$ would be activated to reverse the polarity of the current. More than one anode electrode and more than one cathode electrode may be selected at one time, and thus current can flow through the tissue R between two or more of the electrodes 16. Power for the stimulation circuitry 28 is provided by a compliance voltage VH, as described in further detail in U.S. Patent Application Publication 2013/0289665. Other examples of stimulation circuitries and details of various PDAC and NDAC circuits are disclosed in U.S. Pat. Nos. 6,181,969, 8,606,362, 8,620,436, U.S. Patent Application Publications 2018/0071520 and 2019/0083796. Note that the stimulation circuitry 28 is capable of independently setting the current at any of the electrodes—what is sometimes known as a Multiple Independent Current Control (MICC).

A DC-blocking capacitor Ci 38 is placed in series between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

As noted above, biphasic pulses as shown in FIG. 2A can be useful to recover charge stored on capacitances in the current path and in particular on the DC-blocking capacitors 38. When constant current I is driven during the first phase 30a, the capacitors in the current path (C4 and C5) will store charge at a rate $dV/dt=I/C$, and thus building a voltage across these capacitors (Vc4 and Vc5). When the polarity of this current is reversed during the second phase 30b, this stored charge is recovered, and the voltage across the capacitors preferably returns to zero before the issuance of the next pulse (i.e., before the next phase 30a). Using biphasic pulses in this manner is sometimes referred to as "active" charge recovery, because the charge stored during the first phase 30a is recovered by a current actively driven by the stimulation circuitry 28 during the second phase 30b. It is usually preferred during active charge recovery that the phases 30a and 30b are charge balanced—that is, that the amount of charge passed during the first phase 30a equal the amount of charge passed during the second phase 30b. This can be achieved by setting the current amplitude and the pulse widths to equal values during both phases (|+A|=|−A|; PWa=PWb). However, this is not strictly necessary, and charge balancing can also be achieved if the product of the amplitude and pulse width is equal for both phases (or more generally if the area under their curves is equal).

Stimulation pulses may also be provided using monophasic pulses followed by the use of passive charge recovery, as shown in FIG. 2B. Such monophasic pulses comprise only a single active phase 30a, which is actively driven as before. Because this phase 30a will charge capacitances in the current path as just described, it is again prudent to recover such charge, but this occurs passively without the stimulation circuitry 28 (i.e., the PDACs and NDACs) driving an active current. Specifically, passive charge recovery switches $41_i$ are provided in the stimulation circuitry 28 (FIG. 3). A switch $41_i$ is coupled between each of the electrode nodes ei 39 and a reference potential. In the depicted example, this reference potential comprises the voltage of the battery 14 (Vbat), although another reference potential can be used. After the first pulse phase 30a is issued, one or more of these switches $41_i$ (all, or at least $41_4$ and $41_5$ whose electrodes nodes e4 and e5 were involved in providing the current during the first phase) are closed during a passive charge recovery period 30c (FIG. 2B). This places the capacitors charged during the first phase in parallel between the reference potential (Vbat), and the patient's tissue, R. As a result, and as shown in FIG. 2B, a current pulse of opposite polarity will flow at each electrode as the capacitors discharge, which current will exponentially decay at a rate depending of the values of the capacitances and the resistances inherent in the IPG's circuitry and the tissue R. Preferably, switches $41_i$ are closed during period $30c$ for a duration sufficient to effectively recover all charge that was stored on capacitive elements (e.g., capacitors 38) during the first phase $30a$. At the end of passive charge recovery period, the switches $41_i$ can again be opened. Passive charge recovery is more fully explained in U.S. Patent Application Publications 2018/0071527 and 2018/0140831.

Note that passive charge recovery can also be used with the biphasic pulses shown in FIG. 2A. Thus, a passive charge recovery period $30c$ may follow the second actively-driven phase $30b$. Even if the actively-driven phases $30a$ and $30b$ are designed to be charge balanced, non-idealities may not result in perfect charge balancing, and so providing passive charge recovery during phase $30c$ can be prudent to assure that charge is fully recovered before the issuance of a next pulse.

FIG. 4 shows an external trial stimulation environment that may precede implantation of an IPG 10 in a patient. During external trial stimulation, stimulation can be tried on a prospective implant patient without going so far as to implant the IPG 10. Instead, a trial electrode array 17' comprising one or more leads (e.g., one or more percutaneous leads 15 or paddle leads 19) are implanted in the patient's tissue 32 at a target location 34, such as within the spinal column as explained earlier. The proximal ends of the leads of the trial electrode array 17' exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, the trial electrode array 17' is explanted, and a full IPG 10 and electrode array 17 are implanted as described above; if unsuccessful, the trial electrode array 17' is simply explanted.

Like the IPG 10, the ETS 40 can include one or more antennas to enable bi-directional communications with external devices, explained further with respect to FIG. 5. Such antennas can include a near-field magnetic-induction coil antenna $42a$, and/or a far-field RF antenna $42b$, as described earlier. ETS 40 may also include stimulation circuitry able to form the stimulation pulses in accordance with a stimulation program, which circuitry may be similar or identical to the stimulation circuitry 28 present in the IPG 10. ETS 40 may also include a battery (not shown) for operational power.

FIG. 5 shows various external devices that can wirelessly communicate data with the IPG 10 and the ETS 40, including a patient hand-held external controller 45, and a clinician programmer 50. Both of devices 45 and 50 can be used to send a stimulation program to the IPG 10 or ETS 40—that is, to program their stimulation circuitries to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 40. For example, the external controller 45 can have a near-field magnetic-induction coil antenna $47a$ capable of wirelessly communicating with the coil antenna $27a$ or $42a$ in the IPG 10 or ETS 40. The external controller 45 can also have a far-field RF antenna $47b$ capable of wirelessly communicating with the RF antenna $27b$ or $42b$ in the IPG 10 or ETS 40. The external controller 45 can also have controller circuitry 48 such as a microprocessor, microcomputer, an FPGA, other digital logic structures, etc., which is capable of executing instructions an electronic device. Controller circuitry 48 can for example receive patient adjustments to stimulation parameters, and create a stimulation program to be wirelessly transmitted to the IPG 10 or ETS 40.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 5, computing device 51 is shown as a laptop computer that includes typical computer user interface means such as a screen 52, a mouse, a keyboard, speakers, a stylus, a printer, etc., not all of which are shown for convenience. Also shown in FIG. 5 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 40 can depend on the type of antennas included in those devices. If the patient's IPG 10 or ETS 40 includes a coil antenna $27a$ or $42a$, wand 54 can likewise include a coil antenna $56a$ to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40. If the IPG 10 or ETS 40 includes an RF antenna $27b$ or $42b$, the wand 54, the computing device 51, or both, can likewise include an RF antenna $56b$ to establish communication with the IPG 10 or ETS 40 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or stimulation parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which is capable of executing programs in a computing device. Such control circuitry 70, in addition to executing the clinician programmer software 66 and rendering the GUI 64, can also enable communications via antennas 56a or 56b to communicate stimulation parameters chosen through the GUI 64 to the patient's IPG 10.

A portion of the GUI 64 is shown in one example in FIG. 6. One skilled in the art will understand that the particulars of the GUI 64 will depend on where clinician programmer software 66 is in its execution, which may depend on previous GUI selections the clinician has made. FIG. 6 shows the GUI 64 at a point allowing for the setting of stimulation parameters for the patient's IPG 10 or ETS 40. While GUI 64 is shown as operating in the clinician programmer 50, the user interface of the external controller 45 may provide similar functionality.

Shown to the right are interfaces where specific stimulation parameters can be defined for a stimulation program. Values for stimulation parameters relating to the shape of the waveform (A; in this example, current; PW; F) are shown in a waveform parameter interface 84, including buttons the clinician can use to increase or decrease these values. Stimulation parameters relating to the electrodes 16 (the active electrodes and their polarities), are made adjustable in an electrode parameter interface 86. Electrode parameters are also visible and can be manipulated in a leads interface 92 that displays the electrode array 17 (or 17') in generally their proper position with respect to each other, for example, on the left and right sides of the spinal column (only two leads are shown for simplicity). A cursor 94 (or other selection means such as a mouse pointer) can be used to select a particular electrode in the leads interface 92. Buttons in the electrode parameter interface 86 allow the selected electrode (including the case electrode, Ec) to be designated as an anode, a cathode, or off. The electrode parameter interface 86 further allows the relative strength of anodic or cathodic current of the selected electrode to be specified in terms of a percentage, X. This is particularly useful if more than one electrode is to act as an anode or cathode at a given time, as explained in the '038 Publication. In accordance with the example waveforms shown in FIGS. 2A and 2B, as shown in the leads interface 92, electrode E4 has been selected as the only anode to source current, and this electrode receives X=100% of the specified anodic current, +A. Likewise, electrode E5 has been selected as the only cathode to sink current, and this electrode receives X=100% of that cathodic current, −A. Again, more than one electrode can be selected to act as an anode or cathode at one time, with those electrodes sharing the anodic current +A or cathodic current −A. For example, electrodes E3 and E4 can both be selected to act as anode electrodes, with E3 receiving 30% of +A, and E4 receiving 70% of +A. GUI 64 can include other advanced options not shown as well, which for example allow for setting of a duty cycle (on/off time) for the stimulation pulses, setting a ramp-up time over which stimulation pulses will reach its programmed amplitude (A), options to specify the use of biphasic waveforms and/or passive charge recovery, etc.

SUMMARY

A method is disclosed for programming a stimulator device comprising a plurality of electrode nodes, each electrode node configured to be coupled to one of a plurality of electrodes configured to contact a patient's tissue. The method may comprise: programming the stimulator device to provide a repeating sequence of interleaved first and second pulses at at least two of the electrode nodes to create via the first and second pulses a stimulation current through the patient's tissue, wherein, at a first electrode node of the at least two electrode nodes, each first pulse comprises a first monophasic pulse of a first polarity and a first passive charge recovery pulse of a second polarity opposite the first polarity, the first passive charge recovery pulse being configured to recover charge stored during the first monophasic pulse, and wherein, at the first electrode node, each second pulse comprises a second monophasic pulse of the second polarity and a second passive charge recovery pulse of the first polarity, the second passive charge recovery pulse being configured to recover charge stored during the second monophasic pulse.

In one example, the first passive recovery pulse follows immediately after the first monophasic pulse in the first pulse at the first electrode node, and wherein the second passive recovery pulse follows immediately after the second monophasic pulse in the second pulse at the first electrode node. In one example, the first monophasic pulse has a first amplitude and a first pulse width, and wherein the second monophasic pulse has a second amplitude and a second pulse width. In one example, the first and second amplitudes comprise constant current amplitudes. In one example, the first and second amplitudes are equal, and wherein the first and second pulse widths are equal. In one example, the first and second monophasic pulses are charge balanced at the first electrode node. In one example, the first and second monophasic pulses are not charge balanced at the first electrode node. In one example, the stimulator device comprises stimulation circuitry comprising one or more Digital-to-Analog converters (DACs) configured to actively drive the first and second monophasic pulses at the first electrode node. In one example, the stimulation circuitry comprises a plurality of passive recovery switches each coupled between one of the electrode nodes and a reference potential, wherein the first and second passive charge recovery pulses are formed by closing the passive recovery switch coupled to the first electrode node. In one example, the one or more DACs are not configured to actively drive the first and second passive charge recovery pulses. In one example, the one or more DACs comprise one or more positive DACs (PDACs) configured to source a current and one or more negative DACs (NDACs) designed to sink a current, wherein the first monophasic pulses are actively driven at the first electrode node by at least one of the one or more PDACs, and wherein the second monophasic pulses are actively driven at the first electrode node by at least one of the one or more NDACs. In one example, the second pulses are centered in time with the first pulses at the first electrode node. In one example, the first and second pulses do not overlap at the first electrode. In one example, at a second electrode node of the at least two electrode nodes, each first pulse comprises a third monophasic pulse of the second polarity and a third passive charge recovery pulse of the first polarity, the third passive charge recovery pulse being configured to recover charge stored during the third monophasic pulse, wherein, at the second electrode node, each second pulse comprises a fourth monophasic pulse of the first polarity and a fourth passive charge recovery pulse of the second polarity, the fourth passive charge recovery pulse being configured to recover charge stored during the fourth monophasic pulse. In one example, the first and third monophasic pulses are coincident in time, and wherein the second and fourth monophasic pulses are coincident in time. In one example, the first and third passive charge recovery pulses are coincident in time, and wherein the second and fourth passive charge recovery pulses are coincident in time. In one example, the stimulator device further comprises a case for housing the stimulation circuitry, wherein the case is conductive and comprises one of the plurality of electrodes, wherein the second electrode node comprises an electrode node coupled to the conductive case. In one example, an interphase period during which no stimulation current flows intervenes between (i) the first monophasic pulse and the first passive charge recovery pulse in each first pulse, and (ii) the second monophasic pulse and the second passive charge recovery pulse in each second pulse. In one example, the first pulses are issued at a first frequency at the first electrode node and wherein the second pulses are issued at the first frequency at the first electrode node. In one example, the stimulator device comprises at least one implantable lead, wherein at least some of the electrodes are located on the at least one implantable lead. In one example, the first electrode node comprises an electrode node coupled to an electrode located on the at least one implantable lead. In one example, each electrode node is coupled to its associated electrode through a DC-blocking capacitor. In one example, the stimulator device comprises an implantable pulse generator or an external trial stimulator.

A stimulator device is disclosed, which may comprise: a plurality of electrode nodes, each electrode node configured to be coupled to one of a plurality of electrodes configured to contact a patient's tissue; and stimulation circuitry configured by stimulation parameters to provide a repeating sequence of interleaved first and second pulses at at least two of the electrode nodes to create via the first and second pulses a stimulation current through the patient's tissue, wherein, at a first electrode node of the at least two electrode nodes, each first pulse comprises a first monophasic pulse of a first polarity and a first passive charge recovery pulse of a second polarity opposite the first polarity, the first passive charge recovery pulse being configured to recover charge stored during the first monophasic pulse, and wherein, at the first electrode node, each second pulse comprises a second monophasic pulse of the second polarity and a second passive charge recovery pulse of the first polarity, the second passive charge recovery pulse being configured to recover charge stored during the second monophasic pulse.

In one example, the first passive recovery pulse follows immediately after the first monophasic pulse in the first pulse at the first electrode node, and wherein the second passive recovery pulse follows immediately after the second monophasic pulse in the second pulse at the first electrode node. In one example, the first monophasic pulse has a first amplitude and a first pulse width, and wherein the second monophasic pulse has a second amplitude and a second pulse width. In one example, the first and second amplitudes comprise constant current amplitudes. In one example, the first and second amplitudes are equal, and wherein the first and second pulse widths are equal. In one example, the first and second monophasic pulses are charge balanced at the first electrode node. In one example, the first and second monophasic pulses are not charge balanced at the first electrode node. In one example, the stimulation circuitry comprises one or more Digital-to-Analog converters (DACs) configured to actively drive the first and second monophasic pulses at the first electrode node. In one example, the stimulation circuitry comprises a plurality of passive recovery switches each coupled between one of the electrode nodes and a reference potential, wherein the first and second passive charge recovery pulses are formed by closing the passive recovery switch coupled to the first electrode node. In one example, the one or more DACs are not configured to actively drive the first and second passive charge recovery pulses. In one example, the one or more DACs comprise one or more positive DACs (PDACs) configured to source a current and one or more negative DACs (NDACs) designed to sink a current, wherein the first monophasic pulses are actively driven at the first electrode node by at least one of the one or more PDACs, and wherein the second monophasic pulses are actively driven at the first electrode node by at least one of the one or more NDACs. In one example, the second pulses are centered in time with the first pulses at the first electrode node. In one example, the first and second pulses do not overlap at the first electrode. In one example, at a second electrode node of the at least two electrode nodes, each first pulse comprises a third monophasic pulse of the second polarity and a third passive charge recovery pulse of the first polarity, the third passive charge recovery pulse being configured to recover charge stored during the third monophasic pulse, wherein, at the second electrode node, each second pulse comprises a fourth monophasic pulse of the first polarity and a fourth passive charge recovery pulse of the second polarity, the fourth passive charge recovery pulse being configured to recover charge stored during the fourth monophasic pulse. In one example, the first and third monophasic pulses are coincident in time, and wherein the second and fourth monophasic pulses are coincident in time. In one example, the first and third passive charge recovery pulses are coincident in time, and wherein the second and fourth passive charge recovery pulses are coincident in time. In one example, the stimulator device further comprises a case for housing the stimulation circuitry, wherein the case is conductive and comprises one of the plurality of electrodes, wherein the second electrode node comprises an electrode node coupled to the conductive case. In one example, an interphase period during which no stimulation current flows intervenes between (i) the first monophasic pulse and the first passive charge recovery pulse in each first pulse, and (ii) the second monophasic pulse and the second passive charge recovery pulse in each second pulse. In one example, the first pulses are issued at a first frequency at the first electrode node and wherein the second pulses are issued at the first frequency at the first electrode node. In one example, the stimulator device further comprises at least one implantable lead, wherein at least some of the electrodes are located on the at least one implantable lead. In one example, the first electrode node comprises an electrode node coupled to an electrode located on the at least one implantable lead. In one example, each electrode node is coupled to its associated electrode through a DC-blocking capacitor. In one example, the stimulator device comprises an implantable pulse generator or an external trial stimulator.

A non-transitory computer readable medium is disclosed comprising instructions for programming a stimulator device comprising a plurality of electrode nodes, each electrode node configured to be coupled to one of a plurality of electrodes configured to contact a patient's tissue, wherein the instructions when executed are configured perform the following method: programming stimulation circuitry in the stimulator device to provide a repeating sequence of interleaved first and second pulses at at least two of the electrode nodes to create via the first and second pulses a stimulation current through the patient's tissue, wherein, at a first electrode node of the at least two electrode nodes, each first pulse comprises a first monophasic pulse of a first polarity and a first passive charge recovery pulse of a second polarity opposite the first polarity, the first passive charge recovery pulse being configured to recover charge stored during the first monophasic pulse, and wherein, at the first electrode node, each second pulse comprises a second monophasic pulse of the second polarity and a second passive charge recovery pulse of the first polarity, the second passive charge recovery pulse being configured to recover charge stored during the second monophasic pulse.

In one example, the non-transitory computer readable media resides in the stimulator device. In one example, the non-transitory computer readable media resides in an external device used to program the stimulator device. In one example, the first passive recovery pulse follows immediately after the first monophasic pulse in the first pulse at the first electrode node, and wherein the second passive recovery pulse follows immediately after the second monophasic pulse in the second pulse at the first electrode node. In one example, the first monophasic pulse has a first amplitude and a first pulse width, and wherein the second monophasic pulse has a second amplitude and a second pulse width. In one example, the first and second amplitudes comprise constant current amplitudes. In one example, the first and second amplitudes are equal, and wherein the first and second pulse widths are equal. In one example, the first and second monophasic pulses are charge balanced at the first electrode node. In one example, the first and second monophasic pulses are not charge balanced at the first electrode node. In one example, the second pulses are centered in time with the first pulses at the first electrode node. In one example, the first and second pulses do not overlap at the first electrode. In one example, at a second electrode node of the at least two electrode nodes, each first pulse comprises a third monophasic pulse of the second polarity and a third passive charge recovery pulse of the first polarity, the third passive charge recovery pulse being configured to recover charge stored during the third monophasic pulse, wherein, at the second electrode node, each second pulse comprises a fourth monophasic pulse of the first polarity and a fourth passive charge recovery pulse of the second polarity, the fourth passive charge recovery pulse being configured to recover charge stored during the fourth monophasic pulse. In one example, the first and third monophasic pulses are coincident in time, and wherein the second and fourth monophasic pulses are coincident in time. In one example, the first and third passive charge recovery pulses are coincident in time, and wherein the second and fourth passive charge recovery pulses are coincident in time. In one example, the stimulator device further comprising a case for housing the stimulation circuitry, wherein the case is conductive and comprises one of the plurality of electrodes, wherein the second electrode node comprises an electrode node coupled to the conductive case. In one example, an interphase period during which no stimulation current flows intervenes between (i) the first monophasic pulse and the first passive charge recovery pulse in each first pulse, and (ii) the second monophasic pulse and the second passive charge recovery pulse in each second pulse. In one example, the first pulses are issued at a first frequency at the first electrode node and wherein the second pulses are issued at the first frequency at the first electrode node.

A method is disclosed for programming a stimulator device comprising a plurality of electrode nodes, each electrode node configured to be coupled to one of a plurality of electrodes configured to contact a patient's tissue. The method may comprise: receiving at a graphical user interface (GUI) on an external device used to program the stimulation device stimulation parameters for pulses to be produced at at least two of the electrode nodes in the stimulator device, automatically deriving at the external device waveforms from the stimulation parameters, wherein the waveforms comprise interleaved first and second pulses at the at least two electrode nodes, wherein in the automatically derived waveforms, at a first electrode node of the at least two electrode nodes, each first pulse comprises a first monophasic pulse of a first polarity followed by a first passive charge recovery pulse configured to recover charge stored during the first monophasic pulse, and wherein in the automatically derived waveforms, at the first electrode node, each second pulse comprises a second monophasic pulse of a second polarity opposite the first polarity followed by a second passive charge recovery pulse configured to recover charge stored during the second monophasic pulse.

In one example, the stimulation parameters do not independently specify the interleaved first and second pulses. In one example, in the automatically derived waveforms, at a second electrode node of the at least two electrode nodes, each first pulse comprises a third monophasic pulse of the second polarity followed by a third passive charge recovery pulse configured to recover charge stored during the third monophasic pulse, wherein in the automatically derived waveforms, at the second electrode node, each second pulse comprises a fourth monophasic pulse of the first polarity followed by a fourth passive charge recovery pulse configured to recover charge stored during the second monophasic pulse. In one example, the first and third monophasic pulses are coincident in time, and wherein the second and fourth monophasic pulses are coincident in time. In one example, the first and third passive charge recovery pulses are coincident in time, and wherein the second and fourth passive charge recovery pulses are coincident in time. In one example, the method further comprises transmitting the derived waveforms to the stimulator device to produce the pulses at the least two of the electrode nodes. In one example, automatically deriving the waveforms from the stimulation parameters occurs upon receipt at the GUI of a user selection.

A system is disclosed, which may comprise: a stimulator device, comprising a plurality of electrode nodes, each electrode node configured to be coupled to one of a plurality of electrodes configured to contact a patient's tissue; and an external device for programming the stimulator device, comprising a non-transitory computer readable media comprising a software program, wherein the software program when executed on the external device is configured to render a graphical user interface (GUI) on the external device, receive at the (GUI) stimulation parameters for pulses to be produced at at least two of the electrode nodes in the stimulator device, automatically derive waveforms from the stimulation parameters, wherein the waveforms comprise interleaved first and second pulses at the at least two electrode nodes, wherein in the automatically derived waveforms, at a first electrode node of the at least two electrode nodes, each first pulse comprises a first monophasic pulse of a first polarity followed by a first passive charge recovery pulse configured to recover charge stored during the first monophasic pulse, and wherein in the automatically derived waveforms, at the first electrode node, each second pulse comprises a second monophasic pulse of a second polarity opposite the first polarity followed by a second passive charge recovery pulse configured to recover charge stored during the second monophasic pulse.

In one example, the stimulation parameters do not independently specify the interleaved first and second pulses. In one example, in the automatically derived waveforms, at a second electrode node of the at least two electrode nodes, each first pulse comprises a third monophasic pulse of the second polarity followed by a third passive charge recovery pulse configured to recover charge stored during the third monophasic pulse, wherein in the automatically derived waveforms, at the second electrode node, each second pulse comprises a fourth monophasic pulse of the first polarity followed by a fourth passive charge recovery pulse configured to recover charge stored during the second monophasic pulse. In one example, the first and third monophasic pulses are coincident in time, and wherein the second and fourth monophasic pulses are coincident in time. In one example, the first and third passive charge recovery pulses are coincident in time, and wherein the second and fourth passive charge recovery pulses are coincident in time. In one example, the software program when executed on the external device is further configured to transmit the derived waveforms to the stimulator device to produce the pulses at the least two of the electrode nodes. In one example, the GUI includes a user-selectable option to automatically derive the waveforms from the stimulation parameters.

A non-transitory computer readable medium is disclosed comprising instructions for a an external device for programming a stimulator device comprising a plurality of electrode nodes, each electrode node configured to be coupled to one of a plurality of electrodes configured to contact a patient's tissue, wherein the instructions when executed on the external device are configured to perform the following method: providing inputs at a graphical user interface (GUI) on the external device to receive stimulation parameters for pulses to be produced at at least two of the electrode nodes in the stimulator device, automatically deriving at the external device waveforms from the stimulation parameters, wherein the waveforms comprise interleaved first and second pulses at the at least two electrode nodes, wherein in the automatically derived waveforms, at a first electrode node of the at least two electrode nodes, each first pulse comprises a first monophasic pulse of a first polarity followed by a first passive charge recovery pulse configured to recover charge stored during the first monophasic pulse, and wherein in the automatically derived waveforms, at the first electrode node, each second pulse comprises a second monophasic pulse of a second polarity opposite the first polarity followed by a second passive charge recovery pulse configured to recover charge stored during the second monophasic pulse.

In one example, the stimulation parameters do not independently specify the interleaved first and second pulses. In one example, in the automatically derived waveforms, at a second electrode node of the at least two electrode nodes, each first pulse comprises a third monophasic pulse of the second polarity followed by a third passive charge recovery pulse configured to recover charge stored during the third monophasic pulse, wherein in the automatically derived waveforms, at the second electrode node, each second pulse comprises a fourth monophasic pulse of the first polarity followed by a fourth passive charge recovery pulse configured to recover charge stored during the second monophasic pulse. In one example, the first and third monophasic pulses are coincident in time, and wherein the second and fourth monophasic pulses are coincident in time. In one example, the first and third passive charge recovery pulses are coincident in time, and wherein the second and fourth passive charge recovery pulses are coincident in time. In one example, the instructions when executed on the external device further comprise transmitting the derived waveforms to the stimulator device to produce the pulses at the least two of the electrode nodes. In one example, the instructions when executed on the external device further comprise providing a user-selectable option on the GUI to automatically derive the waveforms from the stimulation parameters.

BRIEF DESCRIPTION OF THE DRAWINGS

FIG. 1 shows an Implantable Pulse Generator (IPG) useable for Spinal Cord Stimulation (SC S), in accordance with the prior art.

FIGS. 2A and 2B show examples of stimulation pulses producible by the IPG employing active charge recovery and passive charge recovery respectively, in accordance with the prior art.

FIG. 10 shows an example of a symmetric biphasic waveform preferably useable to provide the lower frequency stimulation of FIG. 9.

FIG. 11 shows a first example of waveforms to mimic the functionality of the biphasic waveform of FIG. 10 but employing the use of monophasic pulses followed by passive charge recovery.

FIGS. 12-15 show other examples of modifications to the waveform of FIG. 11.

FIG. 16 shows use of the waveforms of FIG. 11 to create virtual poles.

FIG. 17 shows an option on the GUI of the external device to allow a clinician to form pulses either as biphasic pulses (FIG. 10), or as monophasic pulses followed by passive charger recovery (FIG. 11).

DETAILED DESCRIPTION

Figure 3:
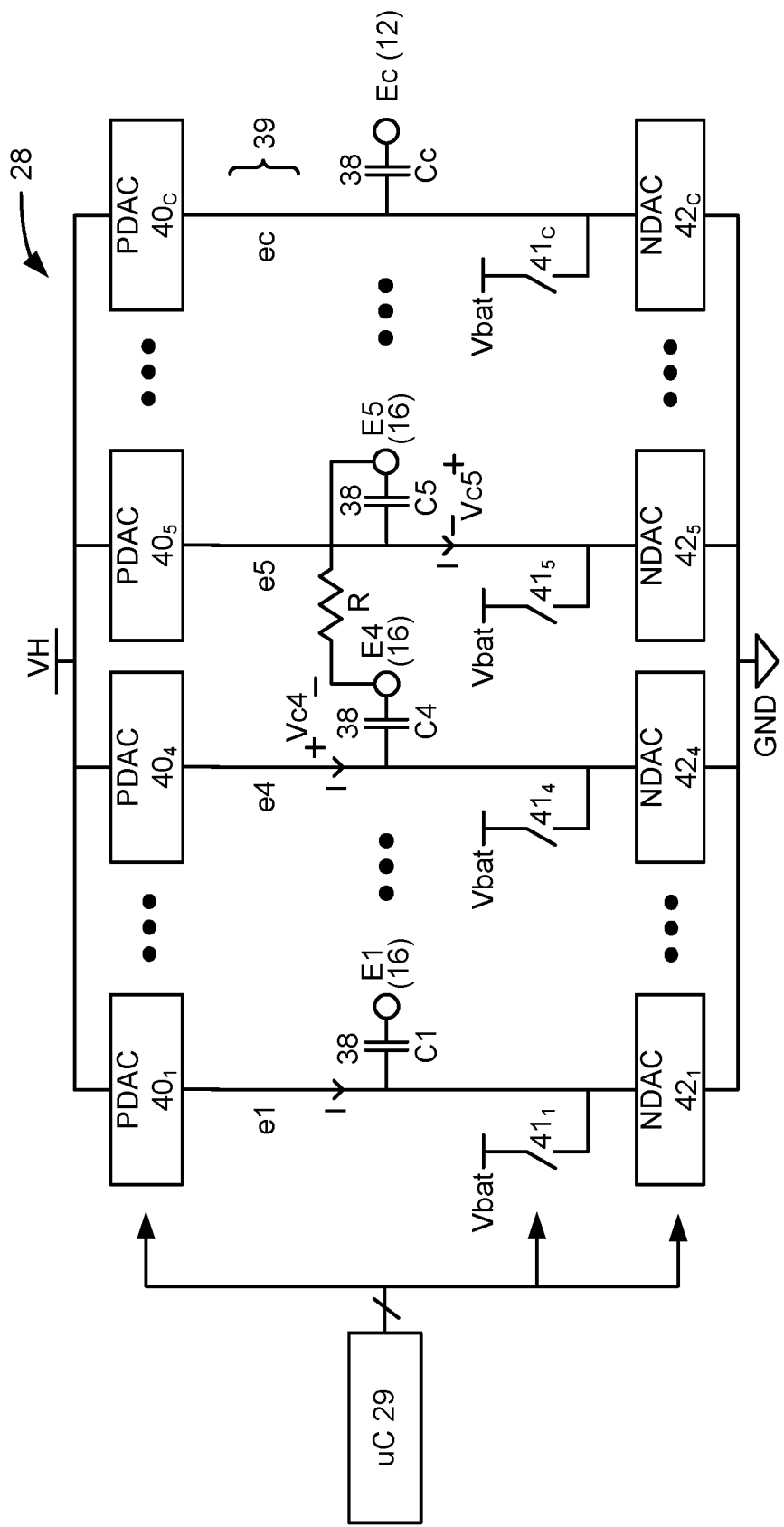
FIG. 3 shows stimulation circuitry used in the IPG to provide stimulation pulses, in accordance with the prior art.

While Spinal Cord Stimulation (SCS) therapy can be an effective means of alleviating a patient's pain, such stimulation can also cause paresthesia. Paresthesia—sometimes referred to a "supra-perception" therapy—is a sensation such as tingling, prickling, heat, cold, etc. that can accompany SCS therapy. Generally, the effects of paresthesia are mild, or at least are not overly concerning to a patient. Moreover, paresthesia is generally a reasonable tradeoff for a patient whose chronic pain has now been brought under control by SCS therapy. Some patients even find paresthesia comfortable and soothing.

Nonetheless, at least for some patients, SCS therapy would ideally provide complete pain relief without paresthesia—what is often referred to as "sub-perception" or sub-threshold therapy that a patient cannot feel. Effective sub-perception therapy may provide pain relief without paresthesia by issuing stimulation pulses at higher frequencies. Unfortunately, such higher-frequency stimulation may require more power, which tends to drain the battery 14 of the IPG 10. See, e.g., U.S. Patent Application Publication 2016/0367822. If an IPG's battery 14 is a primary cell and not rechargeable, high-frequency stimulation means that the IPG 10 will need to be replaced more quickly. Alternatively, if an IPG battery 14 is rechargeable, the IPG 10 will need to be charged more frequently, or for longer periods of time. Either way, the patient is inconvenienced.

In an SCS application, it is desirable to determine a therapeutic stimulation program that will be effective for each patient. A significant part of determining an effective therapeutic stimulation program is to determine a "sweet spot" for stimulation in each patient, i.e., to select which electrodes should be active (E) and with what polarities (P) and relative amplitudes (X %) to recruit and thus treat a neural site at which pain originates in a patient. Selecting electrodes proximate to this neural site of pain can be difficult to determine, and experimentation is typically undertaken to select the best combination of electrodes to provide a patient's therapy. Sweet spot searching to determine the electrodes to use for therapeutic stimulation thereafter is particularly useful in a trial setting after a patient is first implanted with an electrode array, i.e., after receiving their IPG or ETS, but sweet spot searching can also occur at any time during the lifetime of the IPG to optimize therapy.

As described in U.S. Patent Application Publication 2019/0046800 (the '800 Publication), which is hereby incorporated by reference in its entirety, selecting electrodes for a given patient can be even more difficult when sub-perception therapy is used, because the patient does not feel the stimulation, and therefore it can be difficult for the patient to feel whether the stimulation is "covering" his pain and therefore whether selected electrodes are effective. Further, sub-perception stimulation therapy may require a "wash in" period before it can become effective. A wash in period can take up to a day or more, and therefore sub-perception stimulation may not be immediately effective, making electrode selection more difficult.

The '800 Publication discloses that sweet spot searching can therefore preferably occur using supra-perception stimulation, even if the resulting stimulation therapy to be provided following sweet spot searching is sub-perception. Supra-perception therapy by definition allows the patient to feel the stimulation, which enables the patient during sweet spot searching to provide essentially immediate feedback to the clinician whether the paresthesia seems to be well covering his pain without the need for a wash-in period. Further, use of supra-perception stimulation during sweet spot searching ensures that electrodes are determined that well recruit the neural site of a patient's pain. As a result, after the sweet spot search is complete and eventual sub-perception therapy is provided at the determined electrodes, wash in of that sub-perception therapy may not take as long because the electrodes needed for good recruitment have already been confidently determined.

Figure 5:
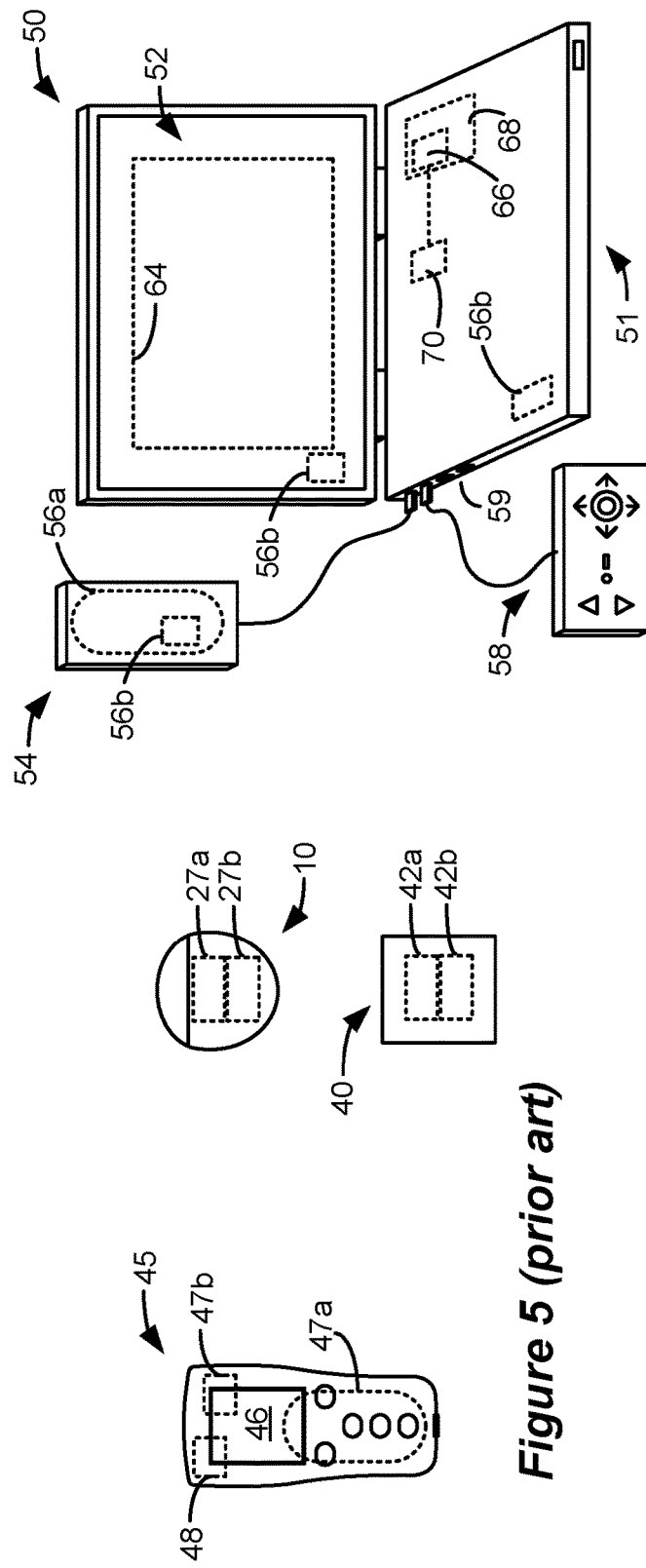
FIG. 5 shows various external devices capable of communicating with and programming stimulation in an IPG and ETS, in accordance with the prior art.
Figure 7:
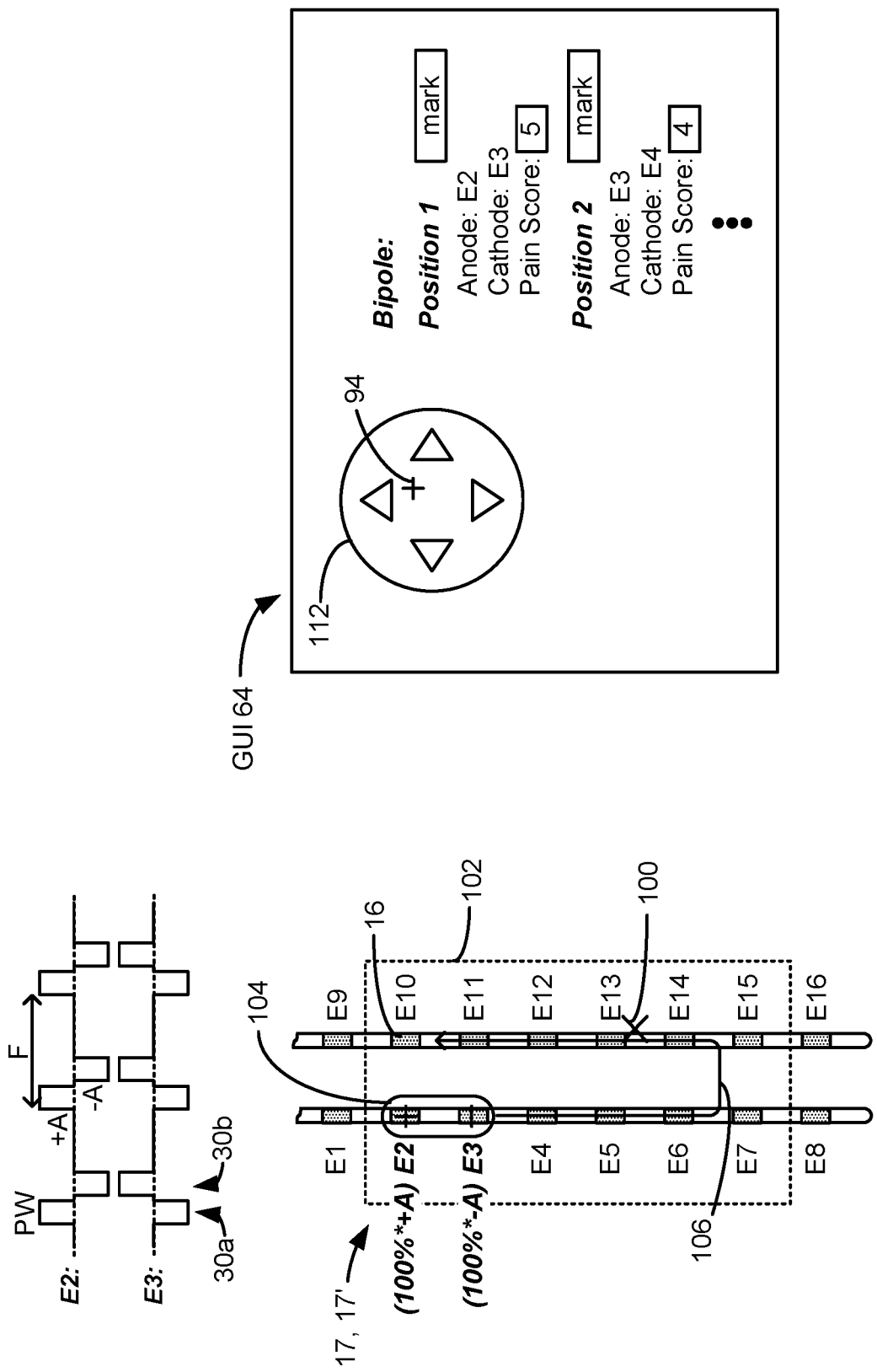
FIG. 7 shows "sweet spot searching" to determine effective electrodes for a patient using a movable supra-perception bipole.

Sweet spot searching as described in the '800 Publication is briefly described in a simple example with respect to FIG. 7. In this example, it is assumed that a pain site 100 is likely within a tissue region 102. Such region 102 may be deduced by a clinician based on the patient symptoms, e.g., by understanding which electrodes are proximate to certain vertebrae (not shown), such as within the T9-T10 interspace. In FIG. 7, a supra-perception bipole 104 is selected and is applied to the patient at a first position (Position 1) in the electrode array 17 or 17'. In this example, the bipole 104 is initially placed in the vicinity of electrodes E2 and E3, with electrode E2 selected as an anode that will source a positive current (+A) to the patient's tissue, and with electrode E3 selected as a cathode that will sink a negative current (−A) from the tissue. The particular stimulation parameters chosen when forming bipole 104 can be selected at the GUI 64 of the clinician programmer 50 or other external device (such as a patient external controller 45) and wirelessly telemetered to the patient's IPG or ETS for execution. The supra-perception bipole 104 is provided to the patient for a short duration, during which the patient provides feedback to the clinician concerning how well the bipole 104 is helping their symptoms. Such patient feedback can comprise a pain scale ranking, which can be entered into the GUI 64 of the clinician programmer 50 (or the patient controller 45; FIG. 5) as shown in FIG. 7, along with information regarding the current position of the bipole 102 as reflected in the position of the anode and cathode electrodes. Pain scale ranking can comprise a scale from 1-10 using a Numerical Rating Scale (NRS) or the Visual Analogue Scale (VAS), with 1 denoting no or little pain and 10 denoting a worst pain imaginable. If necessary, the GUI 64 can include an input to mark, and thus record, the pain ranking and the bipole position.

Figure 6:
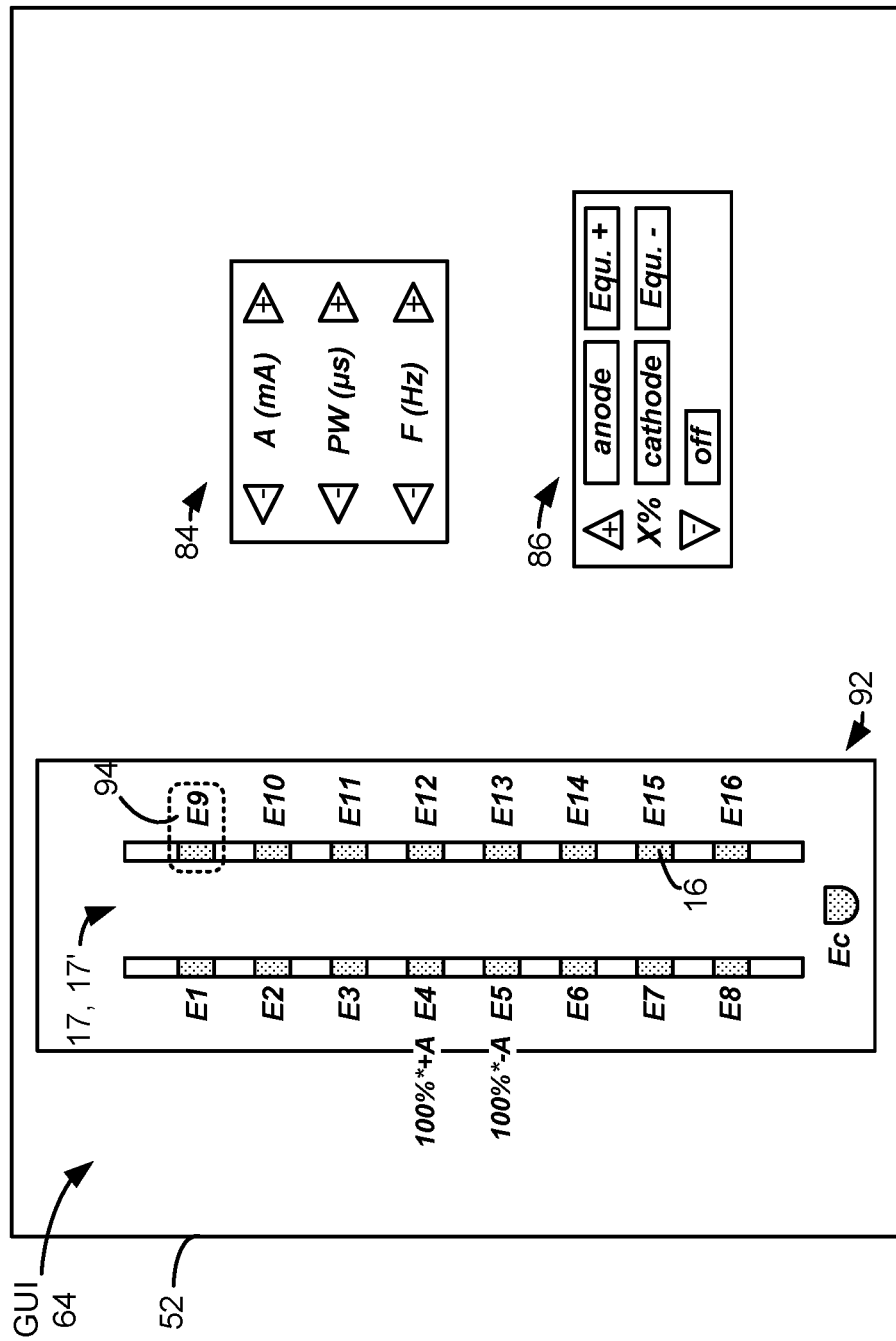
FIG. 6 shows a Graphical User Interface (GUI) of a clinician programmer external device for setting or adjusting stimulation parameters, in accordance with the prior art.

After the bipole 104 is tested at this first location, the bipole 104 can be moved to a different combination of electrodes, such as anode electrode E3 and cathode electrode E4 (Position 2) to again test and record its efficacy. Movement of the bipole can occur in different manners. For example, the GUI can include a dial 112 with arrows that allow the clinician to move the bipole up, down, left, and right in the electrode array 17 or 17', which arrows may be engaged using cursor 94. An accessory device, such as joystick 58 (FIG. 5) can also be used to move the bipole 104. The user may also enter text into the GUI to set the bipole's new position. In the example shown, the bipole 104 is moved down one electrode lead, and up the other, as shown by path 106 in the hope of finding a combination of electrodes that covers the pain site 100. In the example of FIG. 6, given the pain site 100's proximity to electrodes E13 and E14, it might be expected that a bipole 104 at those electrodes will provide the best relief for the patient, as reflected by the patient's pain score rankings. It is not necessary to move the bipole in any particular path 106 during sweet spot searching, and instead the bipole 104 can be moved randomly or in other logical manner, perhaps as guided by the patient's input.

Bipole 104 can be formed in different ways, and as described in the '800 Publication can be formed using virtual poles 108 (i.e., virtual anodes or cathodes) that are not necessarily located at the physical position of the electrodes 16. Virtual poles 108 are discussed further in U.S. Patent Application Publication 2018/0243569 (the '569 Publication), which is incorporated herein by reference in its entirety, and thus virtual poles 108 are only briefly explained here. Forming virtual poles is assisted if the stimulation circuitry 28 used in the IPG or ETS is capable of independently setting the current at any of the electrodes, as explained earlier with reference to FIG. 3.

Figure 4:
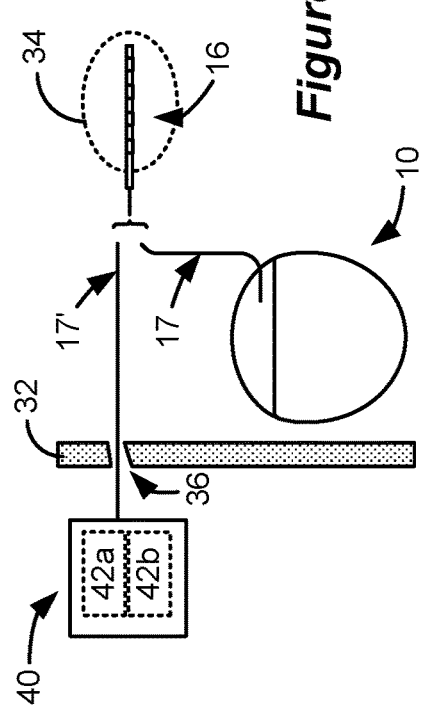
FIG. 4 shows an External Trial Stimulator (ETS) useable to provide stimulation before implantation of an IPG, in accordance with the prior art.
Figure 8:
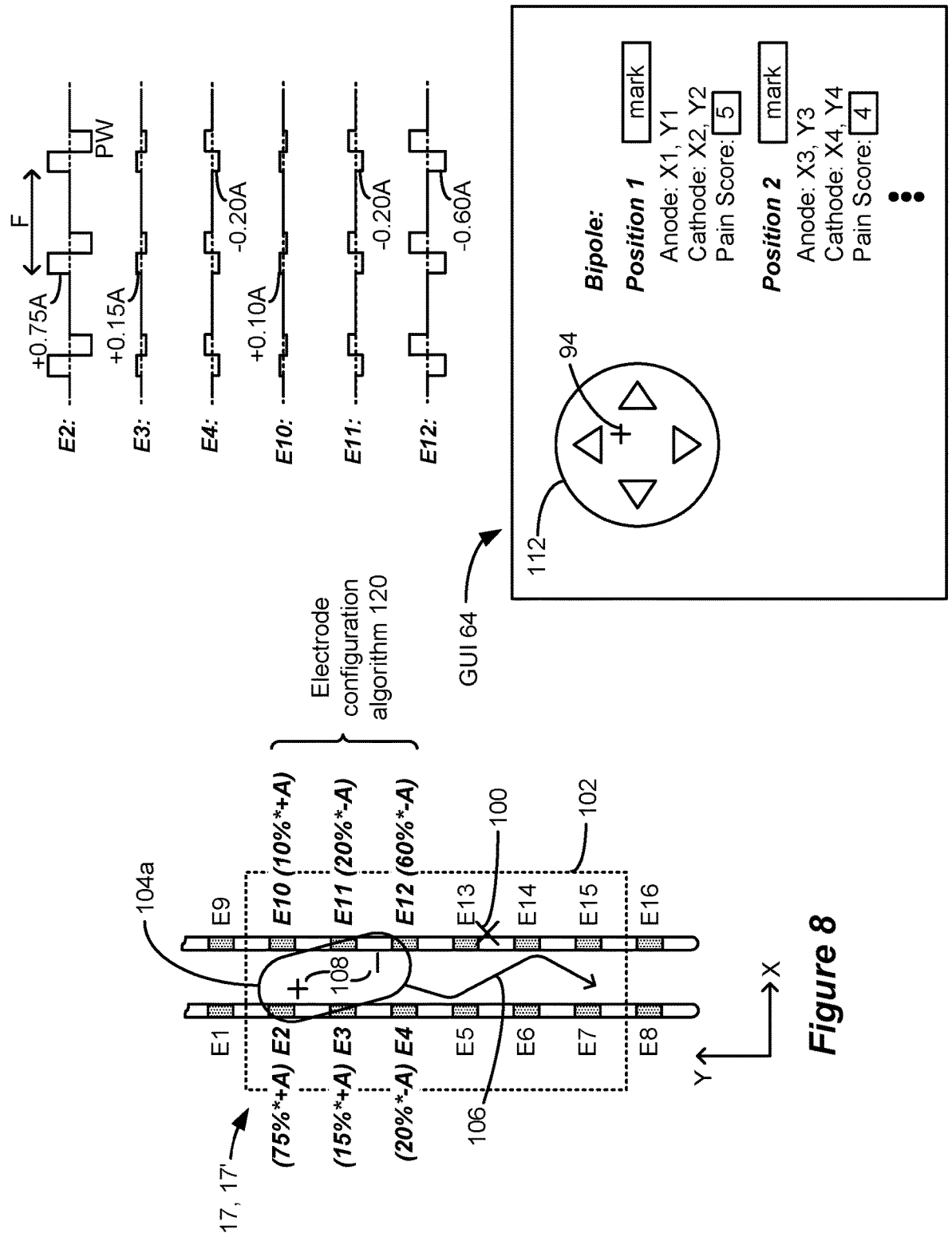
FIG. 8 shows sweet spot searching where the bipole is made from virtual poles that do not correspond to the positions of the electrodes in the electrode array.
Figure 9:
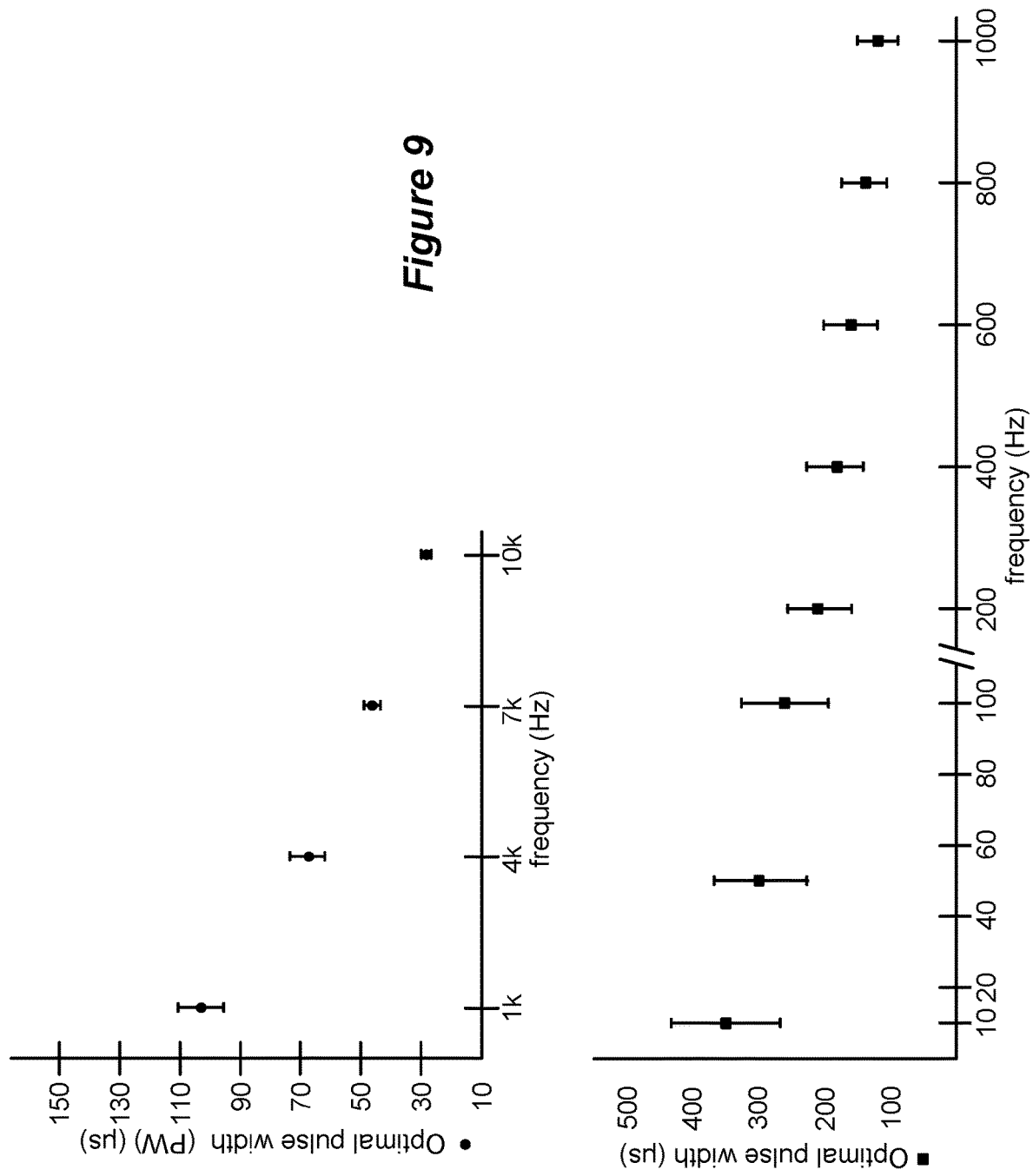
FIG. 9 shows data associating lower frequencies with optimal pulse widths useable to provide sub-perception stimulation in an IPG or ETS.

When a virtual bipole 104a is used and as shown in FIG. 8, the GUI 64 of the clinician programmer 50 (FIG. 4) can be used to define an anode pole (+) and a cathode pole (−) 108 at coordinates X,Y in the electrode array 17 or 17'. As explained in the '569 Publication, an electrode configuration algorithm 120 programmed into control circuitry 70 of the clinician programmer 50 (FIG. 5) can compute from these positions and from other tissue modeling information which physical electrodes 16 will need to be selected and with what relative amplitudes to form the virtual anode and virtual cathode at the designated positions. For example, in FIG. 8, the virtual anode pole is located at a position between electrodes E2, E3 and E10. The electrode configuration algorithm 120 may then calculate based on this position that each of these electrodes (during first pulse phase 30a) will receive an appropriate share (X %) of the total anodic current +A to locate the virtual anode at this position. Since the virtual anode's position is closest to electrode E2, this electrode E2 may receive the largest share of the specified anodic current +A (e.g., 75%*+A). Electrodes E3 and E10 which are proximate to the virtual anode pole's position but farther away receive lesser shares of the anodic current (e.g., 15%*+A and 10%*+A respectively). Likewise, it can be seen that from the designated position of the virtual cathode pole, which is proximate to electrodes E4, E11, and E12, that these electrodes will receive an appropriate share of the specified cathodic current −A (e.g., 20%*−A, 20%*−A, and 60%*−A respectively, again during the first pulse phase 30a). These polarities would then be flipped during the second phases 30b of the pulses, as shown in the waveforms of FIG. 8. In any event, the use of virtual poles in the formation of bipole 104a allows the field in the tissue to be shaped, and many different combinations of electrodes can be tried during the sweet spot search. In this regard, it is not strictly necessary that the (virtual) bipole be moved along an orderly path 106 with respect to the electrodes, and the path may be randomized, perhaps as guided by feedback from the patient.

The '800 Publication explains that once the sweet spot search has been completed and electrodes proximate to the patient's pain site 100 have been determined, sub-perception therapy can then be provided to the patient using those electrodes (or electrode close to them). Significantly, the '800 Publication discloses that effective sub-perception therapy can occur even at lower frequencies (less than or equal to 10 kHz) that use lower amounts of power in the IPG 10 or ETS 40, and that effectiveness at such lower frequencies is achieved when the pulse widths are adjusted to certain values at each frequency. Graphs taken from the '800 Publication are shown in FIG. 10, which shows the relationship between such lower frequencies and pulse widths noticed to provide optimal sub-perception therapy based on empirical testing. The '800 Publication analyzes this data in more depth, including identifying particular relationships (curve fitting) and frequency/pulse width regions indicative of sub-perception effectiveness. The amplitude A of stimulation provided at such frequencies and pulse widths can be titrated down until sub-perception is reached. The reader is assumed familiar with the '800 Publication, and such details are thus not repeated here.

Of particular interest in the '800 Publication is the observation that effective supra-perception sweet spot searching, and effective sub-perception therapy, can be achieved at very low frequencies (less than or equal to 200 Hz). In the '800 Publication, the pulses used during supra-perception sweet spot searching, and/or during sub-perception therapy, are preferably symmetric biphasic pulses. That is, and as shown in FIG. 10, the pulses comprise at least two actively-driven phases 30a and 30b, where the amplitudes A are the same (but of opposite polarity) during each of the phases, and where the pulse widths PW are also equal. (Here it is assumed that a bipole is formed using electrodes E13 and E14 near the site of pain 100 in FIG. 7). It is hypothesized that effectiveness is bolstered because each phase 30a and 30b will tend to actively recruit different neural targets in the patient's tissue. That is, a first group of neural targets is recruited during phase 30a, and a second (possibly overlapping) group of neural targets is recruited during phase 30b. As such, stimulation coverage is expanded. Furthermore, the use of symmetric biphasic pulses is beneficial because, as noted above, such pulses are charge balanced, hence (ideally) recovering all stored charge by the end of the second phase 30b.

However, it can be difficult or impossible in some IPGs or ETSs to form symmetric biphasic pulses at lower frequencies (e.g., <200 Hz). This is because some IPG/ETS manufacturers may not provide the ability to use two-actively driven phases at such low frequencies. Instead, the IPG or ETS may only support, and the GUI 64 of the external device may only allow, for the use of monophasic pulses that use passive charge recovery, as explained earlier with reference to FIG. 2B. While it may be possible to "trick" such devices into forming symmetric biphasic pulses at low frequencies, such tricks are inconvenient and difficult to implement if they are even possible. In short, in the inventors' view, it may be difficult to implement some of the teachings of the '800 Publication when lower frequencies are used either during supra-perception sweet spot searching or sub-perception therapy.

To overcome this problem, the inventors disclose the use of new waveforms for use in an IPG or ETS which can effectively create the desirable effects of actively-driven biphasic pulses at lower frequencies, but through the use of monophasic pulses using passive charge recovery. The waveforms comprise at each electrode interleaved first and second pulses, such that each electrode issues a sequence of a first pulse followed by a second pulse, followed by a first pulse, and so on. Each first pulse comprises a first monophasic pulse of a first polarity having a first amplitude and a first pulse width, and a first passive charge recovery period. The first pulses are preferably issued at a desired frequency, such as less than 200 Hz, as shown to be useful for example in the '800 Publication. Each second pulse comprises a second monophasic pulse of a second polarity opposite the first polarity and having a second amplitude and a second pulse width, and a second passive charge recovery period. The second pulses are issued at the same frequency as the first pulses and each second pulse may be centered in time with respect to a preceding and next first pulse at each electrode. Preferably, the first and second amplitudes and the first and second pulse widths are equal, or at least it is desirable that the opposite-polarity first and second monophasic pulses are charge balanced at each electrode. The first and second monophasic pulses mimic the functionality of a biphasic pulse, with the first monophasic pulse mimicking the functionality of the biphasic pulse's first phase, and the with the second monophasic pulse mimicking the functionality of the biphasic pulse's second phase. Because each of the first and second pulses comprises a monophasic pulse followed by a passive charge recovery period, they are easy to form at low frequencies in traditional IPG or ETS devices.

Such waveforms are shown in a first example in FIG. 11. As just explained, first pulses 130 are issued at a frequency F. This frequency F may be less than 200 Hz for example, as shown to be useful for example in the '800 Publication, although the disclosed waveforms can be used at any desired frequency. Each first pulse 130 includes a monophasic pulse 132 followed by a passive charge recovery period 134 which produces a passive charge recovery pulse. The passive recovery pulse 134 follows immediately after the monophasic pulse 132 in the first pulse at the first electrode node, meaning that it follows with a minimal interphase period, or otherwise in the sense that no pulses are issued in between the two even if the gap in time between them is relatively long. The monophasic pulse 132 is actively driven by the stimulation circuitry 28 (FIG. 3), i.e., by one or more PDACs $40_i$ or NDAC $42_i$ depending whether its polarity is positive or negative. At electrode E13, this monophasic pulse 132 is positive (anodic), having a constant current +A during a pulse width PWa, while at electrode E14 the monophasic pulse is negative (cathodic), having a constant current −A during the pulse width PWa. However, it is not strictly necessary that the monophasic pulses 132 be constant over their pulse widths PWa. Instead, the amplitude of monophasic pulses 132 may be variable. Further, the monophasic pulses 132 can comprise a voltage rather than a current, which voltage may be positive or variable.

The monophasic pulses 132 at each electrode are followed by a passive charge recovery period 134 which results in a pulse that is not actively driven by the stimulation circuitry 28. Instead, during passive charge recovery periods 134, the passive charge recovery switches $41_i$ in the stimulation circuitry 28 (FIG. 3) are closed during the passive charge recovery period 134 (i.e., all switches $41_i$, or at least switches $41_{13}$ and $41_{14}$). Passive charge recovery 134 occurs over a duration PWb. PWb is preferably long enough to allow all stored charge during the monophasic pulse 132 (e.g., +Q at E13, or −Q at E14) to be passively recovered during period 134 (e.g., −Q at E13 or +Q at E14). The duration PWb of the passive charge recovery period 134 may be variable, because the duration needed to fully recover stored charge will depend on the particular capacitances and resistances involved. Although not shown, a short interphase period may separate the monophasic pulses 132 from the passive charge recovery pulse 134 in each first pulse 130.

Second pulses 140 are interleaved with the first pulses 130 at each of the electrodes. The second pulses 140 are preferably the same as the first pulses 130, but of opposite polarity. Thus, the second pulses 140 also include a monophasic pulse 142 followed by a passive charger recovery period 144. At electrode E13, the monophasic pulses 142 are negative (cathodic), having a constant current −A during a pulse width PWa, while at electrode E14 the monophasic pulses 132 are positive (anodic), having a constant current +A during the pulse width PWa. In this example, at each electrode, the amplitude of the monophasic pulses 132 and 142 are the same (A, although differing in polarity) as are their pulse widths PWa, meaning that the monophasic pulses 132 and 142 are symmetric and charge balanced at each electrode. However, this is not strictly necessary, as described in later examples. As before, passive charge recovery periods 144 can be implemented by closing relevant passive charge recovery switches 41k, which can again occur over durations PWb, which again is preferably long enough to allow all stored charge during the monophasic pulse 142 (e.g., −Q at E13, or +Q at E14) to be passively recovered during period 144 (e.g., +Q at E13 or −Q at E14).

Because the second pulses 140 are interleaved with the first pulses 130 at each electrode, they are also issued at each electrode with a frequency of F. Each second pulse 140 may be perfectly centered in time with respect to the first pulses 130 that come before and after at each electrode. In other words, at each electrode, each second pulse 140 may issue a time ta after a preceding first pulse 130, and may issue a time tb before a next first pulse 140. (ta and tb may be measured between the beginning of the monophasic pulses 132 and 142 as shown, although other reference points could be chosen). Each second pulse 140 may be centered in time if ta=tb as shown in FIG. 11, meaning that pulses 130 and 140 issue at each electrode with a periodic frequency of 2F. However, it is not strictly necessary that the second pulses 140 be centered in time with respect to flanking first pulses at each electrodes, as discussed subsequently.

When one compares the biphasic waveform of FIG. 10 with the waveform of FIG. 11, it understandable that the two waveforms should have similar therapeutic efficacy. As noted earlier, the waveforms of FIG. 10 are hypothesized to be effective (particular at lower frequencies and particularly when applying sub-perception therapy) because both actively driven phases 30a and 30b will tend to actively recruit different neural targets in the patient's tissue, thus expanding stimulation coverage in the patient's tissue. This is also true when the pulses 130 and 140 are considered in FIG. 11. Essentially, the actively-driven first phases 30a of the biphasic pulse of FIG. 10 are realized by the monophasic pulses 132 in the first pulses 130 of FIG. 11. Likewise, the actively-driven second phases 30b of the biphasic pulse of FIG. 10 are realized by the monophasic pulses 142 in the second pulses 130 of FIG. 11. Moreover, such stimulation in FIG. 11 occurs at the same effective frequency F as in FIG. 10. Furthermore, like the symmetric biphasic pulses of FIG. 10, the waveforms of FIG. 11 are also charged balanced, and such charge balancing can occur in two respects. First, the monophasic pulses 132 and 142 can be charge balanced at each electrode. Second, each monophasic pulse 132 and 142 can be charged balanced with its associated passive charge recovery phase 134 and 144. In either case, the waveforms of FIG. 11 fully recovery charge at each electrode either within each pulse 130 or 140, or between successive pulses 130 and 140.

Furthermore, because the waveform at each electrode comprises a monophasic pulse followed by a passive charge recovery pulse, such pulses are readily formed in IPGs or ETSs that may otherwise not allow actively-driven biphasic pulses (FIG. 10) to be formed at lower frequencies, F. In this regard, note that IPGs or ETSs normally support the definition of different prescribed pulses in different timing channels (TCs). The use of different timing channels allows more complex therapies to be provided by an IPG or ETS, with each timing channel providing its pulses concurrently with pulses in other timing channels, even if the pulses in such timing channels do not overlap in time. See, e.g., U.S. Pat. No. 9,656,081 describing timing channels in an IPG in further detail). When forming the waveforms of FIG. 11, note that the first pulses 130 can be defined and formed in a first timing channel (TC1), while second pulses 140 can be defined and formed in a second timing channel (TC2). Alternatively, pulses 130 and 140 can be formed in a single timing channel.

Modifications to the waveforms of FIG. 11 are possible, and some modifications are shown in FIGS. 12-16. In FIG. 12, the second pulses 140 are not time centered with respect to the first pulses 130. Instead, the second pulses 140 issue as soon as the first pulses are finished, i.e., as soon as the passive charge recovery period 134 of preceding first pulses 130 is finished. That is, the second pules 140 may issue at a time ta after preceding first pulses 130. ta in this instance will be shorter than tb (the time to a next first pulse 130), and preferably ta is at least long enough to encompass the duration of the monophasic pulse 132 (PWa) and the duration of the passive charge recovery period 134 (PWb). FIG. 13 shown a similar modification, expect that the second pulses 140 issue as late as possible before a next first pulses 130 is started. In this example, the second pulses 140 are started with sufficient time to finish before a next first pulse 130 is issued at a given electrode. This means that the second pulses at started at least a time tb before a next first pulse, meaning that the time tb is at least as long as the durations of the monophasic pulses 142 (PWa) and the passive charge recovery periods 144 (PWb) of the second pulses 140. In this instance, time tb would be shorter than time ta as FIG. 13 shows. Of course, the second pulses 140 can occur anywhere between the extremes shown in FIGS. 12 and 13.

Figure 14:
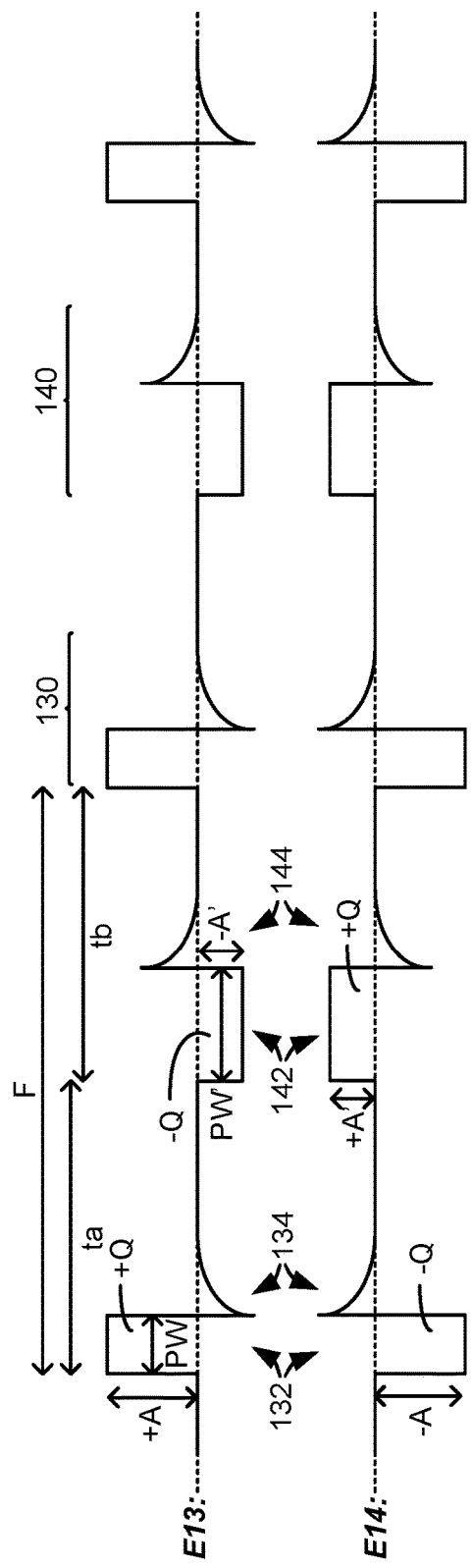

In the modification of FIG. 14, the monophasic portions 132 and 142 of the first and second pulses 130 and 140, while of opposite polarities, are not otherwise symmetric. Specifically in this example, at electrode E13, the monophasic pulses 142 in the second pulses 140 are of longer duration (PW') and a lower amplitude (−A') than the than the monophasic pulses 132 in the first pulses 130 (PW, +A). Even though not symmetric, monophasic pulses 132 and 142 are still charge balanced at each electrode, i.e., +Q=|−Q|, because in this instance PW*+A=PW'*|−A|. As noted earlier, charge balancing of pulses 132 and 142 can occur generally speaking if the area under each of these curves is equal (although of opposite polarity). The situation is the same at electrode E14, although the polarities are flipped.

Figure 15:
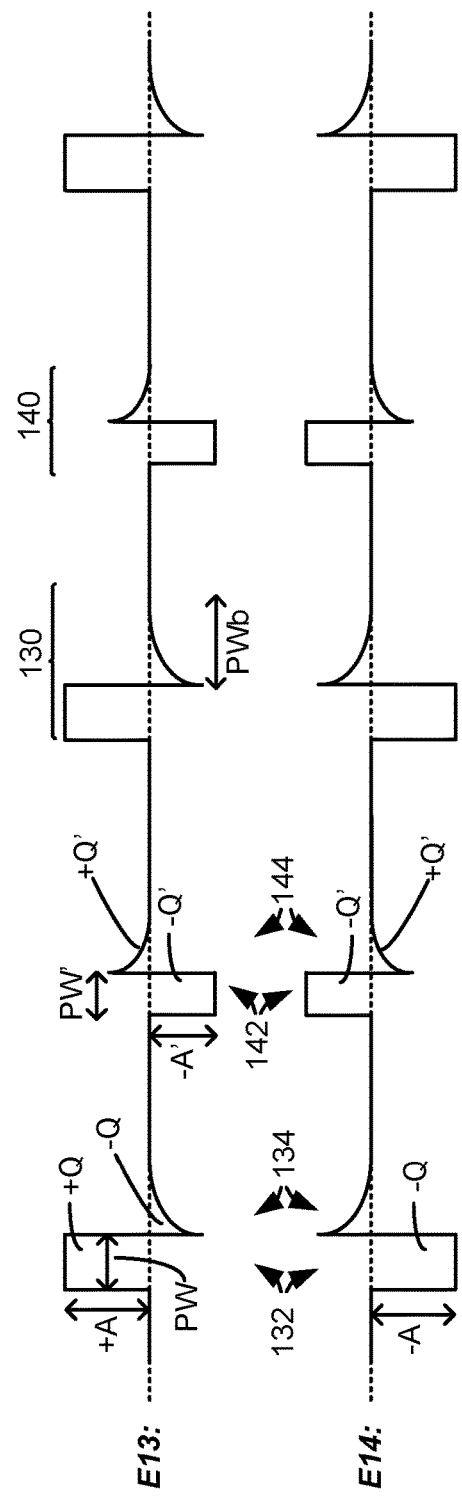

In the modification of FIG. 15, the monophasic pulses 132 and 142 are not charge balanced at each electrode. Specifically, at electrode E13, monophasic pulse 132 has a charge of +Q, while monophasic pulse 142 has a charge of −Q'. In this example, |−Q'| is less than Q, which can be affected by either making the pulse widths of monophasic pulses 142 (PW') smaller than the pulse widths of monophasic pulses 132 (PW), or by making the amplitude of 142 (A') smaller than the amplitude of 132 (A), or both. Even though the monophasic pulses 132 and 142 are not charge balanced, each first and second pulse 130 and 140 is individually charge balanced when their passive recovery periods 134 and 144 are considered. While monophasic pulse 132 provide a charge of +Q, passive recovery period 134 recovers −Q (assuming its duration is sufficient). Likewise, while monophasic pulse 142 provide a charge of −Q', passive recovery period 144 recovers +Q' (again assuming its duration is sufficient). Therefore, each pulse 130 and 140 is individually charged balanced. Again, the situation is the same at electrode E14, although the polarities are flipped.

FIG. 16 shows that the waveforms of FIGS. 11-15 can be provided to more than two electrodes, which as noted earlier is useful to creating stimulation having virtual poles with positions that may not correspond to the physical position of the electrodes 16 in the electrode array. FIG. 16 shows this modification applied to the waveforms of FIG. 11, but similar modification could be made to the waveforms of FIGS. 12-15 as well.

In FIG. 16, a bipole 104a is created as described earlier (FIG. 8), having poles 108. In this example, anodic pole 108 is virtual and its position does not correspond to a physical position of the electrode. Cathodic pole 108 is however positioned at an electrode (E14), although this pole 108 could also be virtually formed at any random position in the electrode array 17 or 17' by fractionalizing the cathodic current −A between different electrodes. Given the virtual anodic pole 108's position relative to electrode E5 and E13, it can be seen that electrode configuration algorithm 120, explained earlier, has operated in the relevant external device (e.g., the clinician programmer 50) to calculate how the anodic current +A should be split between the electrodes to best form the virtual anodic pole at the desired position. Specifically, the electrode configuration algorithm 120 has computed that electrode E13 should receive 75% of the anodic current +A, with electrode E5 receiving the remaining 25%. Note that use of the electrode configuration algorithm 120 isn't strictly necessary. Instead, the user could manually have chosen to use electrodes E13 and E5 as anode electrodes, and could have manually chosen to fractionalize the anodic current at 75% and 25% between them, using the GUI 64 of FIG. 6 for example.

In any event, the resulting waveforms at the electrodes are formed as before, with first pulses 130 having monophasic pulses 132 and passive charge recovery periods 134, and interleaved second pulses 140 having monophasic pulses 142 and passive charge recovery periods 144. The only difference is the resulting amplitude of the pulses at the active electrodes.

As discussed earlier, use of the described waveforms is envisioned as particularly useful when providing therapeutic sub-perception stimulation at lower frequencies. However, use of the disclosed waveforms is not so limited. For example, the disclosed waveforms can be used during sweet spot searching, as discussed earlier with respect to FIGS. 7 and 8. Furthermore, use of the disclosed waveforms is not limited to sub-perception stimulation or any particular frequency or pulse width. Instead, the waveforms can be used to provide supra-perception stimulation more generally. In fact, use of the disclosed waveforms to provide supra-perception stimulation may be particularly useful during sweet spot searching, for the reasons described earlier. The disclosed waveforms, which mimic the functionality of actively-driven biphasic waveforms (FIG. 10), can be used in other stimulation contexts that traditionally use biphasic waveforms.

FIG. 17 shows optional aspects of the GUI 64 of the clinician programmer 50 that can be used to form the waveforms of FIGS. 11-16 having monophasic pulses followed by passive charge recovery. Options has been included to allow the clinician to select to form pulses whose stimulation parameters are otherwise prescribed (e.g., using interfaces 84 and 86) either as biphasic pulses (150) as shown in FIG. 10 for example, or as monophasic pulses using passive charge recovery (152) as shown in FIG. 11 for example. If option 150 is chosen, the software 66 will take the amplitude, pulse width, and frequency information entered, as well as the active electrodes, their polarities, and current fractions (X %), to automatically derive a biphasic waveform with active-driven phases 30a and 30b as explained previously. Once derived, stimulation parameters representative of this waveform can be sent from the clinician programmer 50 to the IPG or ETS for execution by the stimulation circuitry. If as most relevant here option 152 is chosen, the software 66 will take those same parameters and automatically derive a waveform with first and second pulses 130 and 140 of opposite polarities, with each of the pulses 130 and 140 having actively-driven monophasic pulses 132 and 142 followed by passive charge recovery pulses 134 and 144 as previously explained. This is true, even though the entered stimulation parameters (e.g., A, PW, F) do not in and of themselves independently specify interleaved first and second pulses. If necessary, the software 66 may derive these waveforms in a single or multiple (e.g., two) timing channels as explained previously. Once derived, the stimulation parameters representative of this waveform can be sent from the clinician programmer 50 to the IPG or ETS for execution by the stimulation circuitry. Although not shown, the GUI 64 could have other options used to implement the modifications discussed earlier in FIGS. 12-16. For example, other options could allow the amplitude and pulse width of the monophasic pulses 132 and 142 to be separately tailored (e.g., FIGS. 14 and 15), or to adjust the relative timings of pulses 130 and 140 (FIGS. 12 and 13).

Various aspects of the disclosed techniques, including programs implementable in the IPG or ETS, or in external devices such as the clinician programmer or external controller such as software program 66, can be formulated and stored as instructions in a computer-readable media associated with such devices, such as in a magnetic, optical, or solid state memory. The computer-readable media with such stored instructions may also comprise a device readable by the clinician programmer or external controller, such as in a memory stick or a removable disk, and may be wirelessly provided to the IPG or ETS. The computer readable media may reside elsewhere. For example, the computer-readable media may be associated with a server or any other computer device, thus allowing instructions to be downloaded to the clinician programmer system or external controller or to the IPG or ETS, via the Internet for example.

Note that some of the applications to which this present disclosure claims priority, which are incorporated by reference above, are directed to concepts (e.g., selecting optimal stimulation parameters, and in particular stimulation parameters that cause sub-perception at lower frequencies) that are relevant to the waveforms disclosed. Techniques in the present disclosure can also be used in the context of these priority applications.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for programming a stimulator device comprising a plurality of electrode nodes, each electrode node configured to be coupled to one of a plurality of electrodes configured to contact a patient's tissue, the method comprising:
   programming the stimulator device to provide a repeating sequence of interleaved first and second pulses at at least two of the electrode nodes to create via the first and second pulses a stimulation current through the patient's tissue,
   wherein, at a first electrode node of the at least two electrode nodes, each first pulse comprises a first monophasic pulse of a first polarity and a first passive charge recovery pulse of a second polarity opposite the first polarity, the first passive charge recovery pulse being configured to recover charge stored during the first monophasic pulse, and
   wherein, at the first electrode node, each second pulse comprises a second monophasic pulse of the second polarity and a second passive charge recovery pulse of the first polarity, the second passive charge recovery pulse being configured to recover charge stored during the second monophasic pulse,
   wherein the first and second monophasic pulses are charge balanced at the first electrode node.

2. The method of claim 1, wherein the first passive recovery pulse follows immediately after the first monophasic pulse in the first pulse at the first electrode node, and wherein the second passive recovery pulse follows immediately after the second monophasic pulse in the second pulse at the first electrode node.

3. The method of claim 1, wherein the first monophasic pulse has a first amplitude and a first pulse width, and wherein the second monophasic pulse has a second amplitude and a second pulse width.

4. The method of claim 3, wherein the first and second amplitudes comprise constant current amplitudes.

5. The method of claim 4, wherein the first and second amplitudes are equal, and wherein the first and second pulse widths are equal.

6. The method of claim 1, wherein the stimulator device comprises stimulation circuitry comprising one or more Digital-to-Analog converters (DACs) configured to actively drive the first and second monophasic pulses at the first electrode node.

7. The method of claim 6, wherein the stimulation circuitry comprises a plurality of passive recovery switches each coupled between one of the electrode nodes and a reference potential, wherein the first and second passive charge recovery pulses are formed by closing the passive recovery switch coupled to the first electrode node.

8. The method of claim 6, wherein the one or more DACs are not configured to actively drive the first and second passive charge recovery pulses.

9. The method of claim 6, wherein the one or more DACs comprise one or more positive DACs (PDACs) configured to source a current and one or more negative DACs (NDACs) designed to sink a current, wherein the first monophasic pulses are actively driven at the first electrode node by at least one of the one or more PDACs, and wherein the second monophasic pulses are actively driven at the first electrode node by at least one of the one or more NDACs.

10. The method of claim 1, wherein the second pulses are centered in time with the first pulses at the first electrode node.

11. The method of claim 1, wherein the first and second pulses do not overlap at the first electrode.

12. The method of claim 1,
   wherein, at a second electrode node of the at least two electrode nodes, each first pulse comprises a third monophasic pulse of the second polarity and a third passive charge recovery pulse of the first polarity, the third passive charge recovery pulse being configured to recover charge stored during the third monophasic pulse,
   wherein, at the second electrode node, each second pulse comprises a fourth monophasic pulse of the first polarity and a fourth passive charge recovery pulse of the second polarity, the fourth passive charge recovery pulse being configured to recover charge stored during the fourth monophasic pulse.

13. The method of claim 12, wherein the first and third monophasic pulses are coincident in time, and wherein the second and fourth monophasic pulses are coincident in time.

14. The method of claim 13, wherein the first and third passive charge recovery pulses are coincident in time, and wherein the second and fourth passive charge recovery pulses are coincident in time.

15. The method of claim 1, wherein an interphase period during which no stimulation current flows intervenes between (i) the first monophasic pulse and the first passive charge recovery pulse in each first pulse, and (ii) the second monophasic pulse and the second passive charge recovery pulse in each second pulse.

16. The method of claim 1, wherein the first pulses are issued at a first frequency at the first electrode node and wherein the second pulses are issued at the first frequency at the first electrode node.

17. The method of claim 1, wherein the stimulator device comprises at least one implantable lead, wherein at least some of the electrodes are located on the at least one implantable lead, wherein the first electrode node comprises an electrode node coupled to an electrode located on the at least one implantable lead.

18. The method of claim 1, wherein each electrode node is coupled to its associated electrode through a DC-blocking capacitor.

* * * * *